(12) United States Patent
McCoy et al.

(10) Patent No.: US 9,833,541 B2
(45) Date of Patent: Dec. 5, 2017

(54) HEMOSTATIC COMPOSITIONS

(71) Applicants: Baxter International Inc., Deerfield, IL (US); Baxter Healthcare, S.A., Glattpark (Opfikon) (CH)

(72) Inventors: Jill McCoy, Sunnyvale, CA (US); Joseph F. Dwyer, Round Lake, IL (US); Ziping Yang, Buffalo Grove, IL (US)

(73) Assignees: BAXTER INTERNATIONAL INC., Deerfield, IL (US); BAXTER HEALTHCARE S.A., Glattpark (CH)

( * ) Notice: Subject to any disclaimer, the term of this patent is extended or adjusted under 35 U.S.C. 154(b) by 0 days.

(21) Appl. No.: 15/169,872

(22) Filed: Jun. 1, 2016

(65) Prior Publication Data

US 2016/0354511 A1 Dec. 8, 2016

Related U.S. Application Data

(63) Continuation of application No. 13/660,531, filed on Oct. 25, 2012, now abandoned.

(Continued)

(51) Int. Cl.
*A61L 26/00* (2006.01)
*A61M 5/19* (2006.01)
(Continued)

(52) U.S. Cl.
CPC ............ *A61L 26/0052* (2013.01); *A61K 9/06* (2013.01); *A61K 38/17* (2013.01); *A61K 38/38* (2013.01);
(Continued)

(58) Field of Classification Search
None
See application file for complete search history.

(56) References Cited

U.S. PATENT DOCUMENTS

| 2,507,244 A | 5/1950 | Correll |
| 2,558,395 A | 6/1951 | Studer |

(Continued)

FOREIGN PATENT DOCUMENTS

| CN | 1270240 A | 10/2000 |
| EP | 0282316 A2 | 9/1988 |

(Continued)

OTHER PUBLICATIONS

Baxter International; Patients and Caregivers: Therapies; dated Nov. 29, 2011; retrieved on Jul. 27, 2016 from <https://web.archive.org/web/20101129225559/http://www.baxter.com.tw/patients_and_caregivers/therapies/critical.html>.

(Continued)

*Primary Examiner* — Bethany P Barham
*Assistant Examiner* — Dominic Lazaro
(74) *Attorney, Agent, or Firm* — Kilpatrick Townsend & Stockton, LLP

(57) ABSTRACT

The invention discloses a hemostatic composition comprising crosslinked gelatin in particulate form suitable for use in hemostasis, wherein the composition is present in paste form containing 15.0 to 19.5% (w/w), preferably 16.0 to 19.5% (w/w), 16.5 to 19.5% (w/w), 17.0 to 18.5% (w/w) or 17.5 to 18.5% (w/w), more preferred 16.5 to 19.0% (w/w) or 16.8 to 17.8% (w/w), especially preferred 16.5 to 17.5% (w/w), and wherein the composition comprises an extrusion enhancer.

28 Claims, 8 Drawing Sheets

Related U.S. Application Data

(60) Provisional application No. 61/552,270, filed on Oct. 27, 2011.

(51) Int. Cl.
  *A61K 38/17* (2006.01)
  *A61K 38/48* (2006.01)
  *A61K 38/38* (2006.01)
  *A61L 24/10* (2006.01)
  *A61K 9/06* (2006.01)

(52) U.S. Cl.
  CPC ........ *A61K 38/4833* (2013.01); *A61L 24/104* (2013.01); *A61L 24/108* (2013.01); *A61M 5/19* (2013.01); *A61L 2400/04* (2013.01); *A61L 2400/06* (2013.01)

(56) References Cited

U.S. PATENT DOCUMENTS

| | | |
|---|---|---|
| 3,089,815 A | 5/1963 | Kupelwieser et al. |
| 4,006,220 A | 2/1977 | Gottlieb |
| 4,013,078 A | 3/1977 | Field |
| 4,124,705 A | 11/1978 | Rothman et al. |
| 4,164,559 A | 8/1979 | Miyata et al. |
| 4,179,400 A | 12/1979 | Tsao et al. |
| 4,265,233 A | 5/1981 | Sugitachi et al. |
| 4,291,013 A | 9/1981 | Wahlig et al. |
| 4,292,972 A | 10/1981 | Pawelchak et al. |
| 4,298,598 A | 11/1981 | Schwarz et al. |
| 4,300,494 A | 11/1981 | Graiff et al. |
| 4,347,234 A | 8/1982 | Wahlig et al. |
| 4,362,567 A | 12/1982 | Schwarz et al. |
| 4,377,572 A | 3/1983 | Schwarz et al. |
| 4,424,208 A | 1/1984 | Wallace et al. |
| 4,442,655 A | 4/1984 | Stroetmann |
| 4,453,939 A | 6/1984 | Zimmerman et al. |
| 4,482,386 A | 11/1984 | Wittwer et al. |
| 4,515,637 A | 5/1985 | Cioca |
| 4,536,387 A | 8/1985 | Sakamoto et al. |
| 4,540,410 A | 9/1985 | Wood et al. |
| 4,543,332 A | 9/1985 | Jao et al. |
| 4,554,156 A | 11/1985 | Fischer |
| 4,600,574 A | 7/1986 | Lindner et al. |
| 4,640,834 A | 2/1987 | Eibl et al. |
| 4,655,211 A | 4/1987 | Sakamoto et al. |
| 4,746,514 A | 5/1988 | Warne |
| 4,749,689 A | 6/1988 | Miyata et al. |
| 4,803,075 A | 2/1989 | Wallace et al. |
| 4,818,517 A | 4/1989 | Kwee et al. |
| 4,832,686 A | 5/1989 | Anderson |
| 4,837,285 A | 6/1989 | Berg et al. |
| 4,885,161 A | 12/1989 | Cornell |
| 4,891,359 A | 1/1990 | Saferstein et al. |
| 4,925,677 A | 5/1990 | Feijen |
| 4,946,870 A | 8/1990 | Partain, III et al. |
| 5,007,916 A | 4/1991 | Linsky et al. |
| 5,017,229 A | 5/1991 | Burns et al. |
| 5,023,082 A | 6/1991 | Friedman et al. |
| 5,041,292 A | 8/1991 | Feijen |
| 5,061,274 A | 10/1991 | Kensey |
| 5,061,492 A | 10/1991 | Okada et al. |
| 5,080,893 A | 1/1992 | Goldberg et al. |
| 5,108,421 A | 4/1992 | Fowler |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro |
| 5,162,430 A | 11/1992 | Rhee et al. |
| 5,165,938 A | 11/1992 | Knighton |
| 5,178,883 A | 1/1993 | Knighton |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,352,715 A | 10/1994 | Wallace et al. |
| 5,356,614 A | 10/1994 | Sharma |
| 5,384,333 A | 1/1995 | Davis et al. |
| 5,385,606 A | 1/1995 | Kowanko |
| 5,399,361 A | 3/1995 | Song et al. |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Alleyne |
| 5,447,966 A | 9/1995 | Hermes et al. |
| 5,478,352 A | 12/1995 | Fowler |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,614,587 A | 3/1997 | Rhee et al. |
| 5,618,551 A | 4/1997 | Tardy et al. |
| 5,648,506 A | 7/1997 | Desai et al. |
| 5,658,592 A | 8/1997 | Tanihara et al. |
| 5,667,839 A | 9/1997 | Berg |
| 5,672,336 A | 9/1997 | Sharma |
| 5,674,275 A | 10/1997 | Tang et al. |
| 5,690,675 A | 11/1997 | Sawyer et al. |
| 5,698,213 A | 12/1997 | Jamiolkowski et al. |
| 5,714,370 A | 2/1998 | Eibl et al. |
| 5,752,974 A | 5/1998 | Rhee et al. |
| 5,770,229 A | 6/1998 | Tanihara et al. |
| 5,853,749 A | 12/1998 | Hobbs |
| 5,856,356 A | 1/1999 | Tsouderos et al. |
| 5,861,043 A | 1/1999 | Carn |
| 5,874,500 A | 2/1999 | Rhee et al. |
| 5,902,832 A | 5/1999 | Van Bladel et al. |
| 5,908,054 A | 6/1999 | Safabash et al. |
| 5,931,165 A | 8/1999 | Reich et al. |
| 5,959,735 A | 9/1999 | Maris et al. |
| 5,997,895 A | 12/1999 | Narotam et al. |
| 6,056,970 A | 5/2000 | Greenawalt et al. |
| 6,063,061 A * | 5/2000 | Wallace .............. A61L 24/0015 424/423 |
| 6,066,325 A | 5/2000 | Wallace et al. |
| 6,110,484 A | 8/2000 | Sierra |
| 6,129,761 A | 10/2000 | Hubbell |
| 6,132,759 A | 10/2000 | Schacht et al. |
| 6,166,130 A | 12/2000 | Rhee et al. |
| 6,179,872 B1 | 1/2001 | Bell et al. |
| 6,277,394 B1 | 8/2001 | Sierra |
| 6,312,474 B1 | 11/2001 | Francis et al. |
| 6,312,725 B1 | 11/2001 | Wallace et al. |
| 6,328,229 B1 | 12/2001 | Duronio et al. |
| 6,458,386 B1 | 10/2002 | Schacht et al. |
| 6,458,889 B1 * | 10/2002 | Trollsas .............. A61L 24/043 525/419 |
| 6,495,127 B1 | 12/2002 | Wallace et al. |
| 6,624,245 B2 | 9/2003 | Wallace et al. |
| 6,706,690 B2 | 3/2004 | Reich et al. |
| 6,831,058 B1 | 12/2004 | Ikada et al. |
| 7,320,962 B2 | 1/2008 | Reich et al. |
| 7,435,425 B2 | 10/2008 | Qian et al. |
| 7,547,446 B2 | 6/2009 | Qian et al. |
| 7,871,637 B2 | 1/2011 | Qian et al. |

(56) References Cited

U.S. PATENT DOCUMENTS

| | | | |
|---|---|---|---|
| 8,303,981 | B2 | 11/2012 | Wallace et al. |
| 8,357,378 | B2 | 1/2013 | Wallace et al. |
| 8,852,558 | B2 | 10/2014 | Montes et al. |
| 2002/0165337 | A1 | 11/2002 | Wallace et al. |
| 2002/0193448 | A1 | 12/2002 | Wallace et al. |
| 2003/0064109 | A1 | 4/2003 | Qian et al. |
| 2004/0147465 | A1 | 7/2004 | Jiang et al. |
| 2005/0284809 | A1* | 12/2005 | Looney .............. A61L 24/0036 210/502.1 |
| 2006/0147492 | A1 | 7/2006 | Hunter et al. |
| 2006/0167561 | A1 | 7/2006 | Odar et al. |
| 2008/0085316 | A1 | 4/2008 | Qian et al. |
| 2008/0091277 | A1 | 4/2008 | Deusch et al. |
| 2008/0286376 | A1 | 11/2008 | Qian et al. |
| 2009/0142396 | A1 | 6/2009 | Odar et al. |
| 2010/0028309 | A1 | 2/2010 | Odar et al. |
| 2010/0063459 | A1* | 3/2010 | Preiss-Bloom ....... A61L 15/325 604/265 |
| 2010/0292717 | A1 | 11/2010 | Petter-Puchner et al. |
| 2010/0318048 | A1 | 12/2010 | Hoefinghoff et al. |
| 2012/0207813 | A1 | 8/2012 | Rhee et al. |
| 2013/0108671 | A1 | 5/2013 | McCoy et al. |

FOREIGN PATENT DOCUMENTS

| | | |
|---|---|---|
| EP | 0376931 A1 | 7/1990 |
| EP | 0132983 B2 | 12/1991 |
| EP | 0493387 B1 | 7/1992 |
| EP | 0891193 B1 | 1/1999 |
| EP | 0612252 B1 | 5/1999 |
| EP | 0927053 A1 | 7/1999 |
| EP | 1084720 A1 | 3/2001 |
| EP | 1283063 A1 | 2/2003 |
| EP | 1484070 A1 | 12/2004 |
| EP | 1414370 B1 | 4/2007 |
| EP | 1803417 A1 | 4/2007 |
| JP | 51-125156 | 11/1976 |
| JP | 59-113889 | 6/1984 |
| JP | 05-308969 | 11/1993 |
| JP | 07090241 A | 4/1995 |
| JP | 08-024325 | 1/1996 |
| JP | 9-504719 | 5/1997 |
| KR | 10-1991-0007847 B1 | 10/1991 |
| WO | 86/00912 A1 | 2/1986 |
| WO | 92/21354 A1 | 12/1992 |
| WO | 92/22252 A1 | 12/1992 |
| WO | 94/27630 A1 | 12/1994 |
| WO | 95/12371 A1 | 5/1995 |
| WO | 95/15747 A1 | 6/1995 |
| WO | 96/04025 A1 | 2/1996 |
| WO | 96/06883 A1 | 3/1996 |
| WO | 96/10374 A1 | 4/1996 |
| WO | 96/10428 A1 | 4/1996 |
| WO | 96/14368 A1 | 5/1996 |
| WO | 96/39159 A1 | 12/1996 |
| WO | 97/22371 A1 | 6/1997 |
| WO | 97/37694 A1 | 10/1997 |
| WO | 98/08550 A1 | 3/1998 |
| WO | 99/13902 A1 | 3/1999 |
| WO | 02/22059 A1 | 3/2002 |
| WO | 02/22184 A2 | 3/2002 |
| WO | 02/070594 A2 | 9/2002 |
| WO | 03/007845 A1 | 1/2003 |
| WO | 2004/108179 A1 | 12/2004 |
| WO | 2006/031358 A2 | 3/2006 |
| WO | 2006/118460 A1 | 11/2006 |
| WO | 2007/001926 A2 | 1/2007 |
| WO | 2007/137839 A2 | 12/2007 |
| WO | 2007/137839 A3 | 12/2007 |
| WO | 2008/016983 A2 | 2/2008 |
| WO | 2008/076407 A2 | 6/2008 |

OTHER PUBLICATIONS

Letter dated Aug. 11, 2015 for U.S. Appl. No. 13/660,531, filed Oct. 25, 2012; all pages.

Office Action dated May 28, 2015 for International Application No. PCT/EP2012/071136 filed Oct. 25, 2012; all pages.

Letter dated Jul. 30, 2015 for U.S. Appl. No. 14/114,385, filed May 27, 2014; all pages.

Ansell et al., "Gelfoam and Autologous Clot Embolization: Effect on Coagulation." *Investigative Radiology* vol. 13 (1978): pp. 115-120.

Barrow, D.L., et al.; "The Use of Greater Omentum Vascularized Free Flaps for Neurosurgical Disorders Requiring Reconstruction." *Journal of Neurosurgery*, vol. 60 (Feb. 1984): pp. 305-311.

Barton, et al., "Fibrin Glue as a Biologic Vascular Patch—A Comparative Study." (abstract posted at http://www.ncbi.nlm.nih.gov/ on Jan. 3, 2001) *Journal Surgical Research* vol. 40.5 (1986): pp. 510-513.

Baxter product brochure for TissuFleece E, TissuCone E and TissuFoil E (2003).

Baxter Product Catalogue; Collagen; 4 pages (2006).

Baxter, "GentaFleece Collagen Fleece—Version 5 : Collagen Sponge with antibiotic protection for surgical use," Retrieved from http://www.advancingbiosurgery.com/e_EU/downloads/ifu_gentafleece.pdf, Mar. 2002, 2 pages. English portion second column of first page.

Boyers, et al., "Reduction of Postoperative Pelvic Adhesions in the Rabbit with Gore-Tex Surguical Membrane," *Fertility and Sterility* vol. 49.6 (1988): pp. 1066-1070.

Bruck, S. D., Ed., *Controlled Drug Delivery*. CRC Press, Boca Raton, FL (1983) A title page and table of contents.

Cantor, et al., "Gelfoam and Thrombin in Gastrointestinal Bleeding: An Experimental Study." (1950): pp. 890-893.

Cantor, et al., "Gelfoam and Thrombin in Treatment of Massive Gastroduodenal Hemmorhage: A Preliminary Report." *The American Journal of Surgery* (1950): pp. 883-887.

Cantor, et al., "Gelfoam and Thrombin in Treatment of Massive Upper Gastroduodenal Hemorrhage." *The American Journal of Surgery* (1951): pp. 230-235.

Chaplin, J.M., et al., "Use of an Acellular Dermal Allograft for Dural Replacement: An Experimental Study." *Neurosurgery* vol. 45.2 (Aug. 1999): pp. 320-327.

Cheung, David T., et al., "Mechanism of crosslinking of proteins by glutaraldehyde IV: In Vitro and In Vivo stability of a crosslinked collagen matrix." *Connective Tissue Research*, vol. 25.1 (1990): pp. 27-34.

Christensen, et al., "Qualitative Description of the Wurster-Based Fluid-Bed Coating Process." *Drug Development and Industrial Pharmacy* vol. 23.5 (1997): pp. 451-463.

Collins, et al., "Enemata of Gelfoam-Milk Suspension Combined with Thrombin Solution to Control Massive Hemorrhage Following Anorectal Surgery." *American Journal of Proctology* vol. 2 (1951): pp. 60-63.

Collins, Ronald et al., "Use of Collagen Film as a Dural Substitute: Preliminary Animal Studies." *Journal of Biomedical Materials Research* vol. 25 (1991): pp. 267-276.

Edgerton, et al., "Vascular Hamartomas and Hemangiomos: Classification and Treatment." *Southern Medical Journal* vol. 75.12 (1982): pp. 1541-1547.

Filippi, R., et al., "Bovine Pericardium for Duraplasty: Clinical Results in 32 Patients." *Neurosurgical Review* vol. 20 (2001): pp. 103-107.

Gibble, et al., "Fibrin glue: the perfect operative sealant?" *Transfusion* vol. 30.8 (1990): pp. 741-747.

Guoping, Chen, et al., "Scaffold Design for Tissue Engineering." *Macromolecular Bioscience* (2002): pp. 67-77.

Heller, et al., "Release of Norethindrone from Poly(Ortho Esters)." *Polymer Engineering Science* vol. 21 (1981): pp. 727-731.

(56) References Cited

OTHER PUBLICATIONS

Hieb, Lee D., et al., "Spontaneous Postoperative Cerebrospinal Fluid Leaks Following Application of Anti-Adhesion Barrier Gel." *Spine* vol. 26.7 (2001): pp. 748-751.

Hood, et al., "Efficacy of Topical Hemostat Floseal Matrix in Vascular Surgery." 24th World Congress of the International Society for Cardiovascular Surgery (Sep. 12-16, 1999), 2 pages total.

Hotz, et al., "Collagen and Fibrin as Biologic Binders from Granular Hydroxyapatite." (abstract posted at http://www.ncbi.nlm.nih.gov/ on Jan. 3, 2001) *Dtsh. Z. Mund. Kiefer Geichtshir*. vol. 13.4 (1989): pp. 296-300.

Jeong, et al., "Biodegradable Block Copolymers as Injectible Drig-Delivery Systems." *Nature* vol. 388 (1997): pp. 860-862.

Jonas, Richard A., et al., "A new sealant for knitted Dacron prostheses: Minimally cross-linked gelatin." *Journal of Vascular Surgery* vol. 7.3 (1988): pp. 414-419.

Kim, Kee D., et al., "Reduction in Leg Pain and Lower-Extremity Weakness with Oxiplex/SP Gel for 1 Year after Laminectomy, Laminotomy, and Discectomy." *Neurosurgical Focus* vol. 17.1 (2004): pp. 1-6.

Kline, D.G., "Dural Replacement with Resorbable Collagen." *Archives of Surgery* vol. 91 (Dec. 1965): pp. 924-929.

Knopp, U., "A new collagen foil versus a cadaveric dura graft for dural defects—a comparative animal experimental study." EANS—12th European Congress of Neurosurgery, Lisbon (Sep. 7-12, 2003): pp. 663-666.

Kofidis, T., et al., "Clinically established Hemostatis Scaffold (Tissue Fleece) as Biomatrix in Tissue- and organ-engineering research." *Tissue Engineering* vol. 9.3 (2003): pp. 517-523.

Krill, et al., "Topical Thrombin and Powdered Gelfoam: An Efficient Hemostatic Treatment for Surgery." *Journal—Tennessee State Dental Association* vol. 66.2 (1986): pp. 26-27.

Kuhn, J., et al., "Bilateral Subdural Haemotomata and Lumbar Pseudomeningocele Due to a Chronic Leakage of Liquor Cerebrospinalis after a Lumbar Disectomy with the Application of ADCON-L Gel", *Journal of Neurology, Neurosurgery & Psychiatry* vol. 76 (2005): pp. 1031-1033.

Langer, et al., "Chemical and Physical Structure of Polymers as Carriers for Controlled Release of Bioactive Agents: A Review" *Journal of Macromolecular Science, Reviews on Macromolecular Chemistry and Physics* vol. C23.1 (1983): pp. 61-126.

Laquerriere, A., et al., "Experimental Evaluation of Bilayered Human Collagen as a Dural Substitute." *Journal of Neurosurgery* vol. 78 (1993): pp. 487-491.

Larson, Paul O., "Topical Hemostatic Agents for Dermatologic Surgery." *The Journal of Dermatologic Surgery and Oncology* vol. 14.6 (1988): pp. 623-632.

Le, A. X., et al., "Unrecognized Durotomy After Lumbar Discectomy: A Report of Four Cases Associated with the Use of ADCON-L." *Spine* vol. 26.1, (2001): pp. 115-118.

Lee, J.F., et al., "Experimental Evaluation of Silicone-Coated Dacron and Collagen Fabric-Film Laminate as Dural Substitutes." *Journal of Neurosurgery* vol. 27 (1967): pp. 558-564.

Leong, et al., "Polyanhydrides for Controlled Release of Bioactive Agents." *Biomaterials* vol. 7 (1986): pp. 364-371.

Leong, et al., "Polymeric Controlled Drug Delivery." *Advanced Drug Delivery Reviews* vol. 1 (1987): pp. 199-233.

Maok, "Hemostatic Agents:Adjuncts to Control Bleeding." *Today's O. R. Nurse* vol. 13.11 (1991): pp. 6-10.

Masar, et al., "Synthesis of Polyurethanes and Investigation of their Hydrolytic Stability." *Journal of Polymer Science: Polymer Symposium* vol. 66 (1979): pp. 259-268.

Matsumoto, K., et al., "A Gelatin Coated Collagen-Polyglycolic Acid Composite Membrane as a Dural Substitute." *American Society for Artificial Internal Organs Journal* (2001): pp. 641-645.

Maurer, P.K., et al., "Vicryl (Polyglactin 910) Mesh as a Dural Substitute." *Journal of Neurosurgery* vol. 63 (Sep. 1985): pp. 448-452.

McClure, et al., "Massive Gastroduodenal Hemorrhage: Treatment with Powdered Gelfoam and Buffered Thrombin Solution." *Surgery* vol. 32 (1952): pp. 630-637.

McPherson, J. M., et al., "An examination of the biologic response to injectable, glutaraldehyde cross-linked collagen implants." *Journal of Biomedical Materials Research* vol. 20.1 (1986): pp. 93-107.

McPherson, J. M., et al., "The preparation and physiochemical characterization of an injectable form of reconstituted, glutaraldehyde cross-linked, bovine corium collagen." Journal of Biomedical Materials Research vol. 20.1 (1986): pp. 79-92.

McPherson, John M., et al., "The Effects of Heparin on the Physiochemical Properties of Reconstituted Collagen." *Collagen and Related Research* vol. 8.1 (1988): pp. 65-82.

Meddings, N., et al., "Collagen Vicryl—A New Dural Prosthesis," *Acta Neurochir*. vol. 117 (1992): pp. 53-58.

Mello, L.R., et al., "Duraplasty with Biosynthetic Cellulose: An Experimental Study." *Journal of Neurosurgery* vol. 86 (Jan. 1997): pp. 143-150.

Narotam, P.K., et al., "A Clinicopathological Study of Collagen Sponge as a Dural Graft in Neurosurgery." *Journal of Neurosurgery* vol. 82 (Mar. 1995): pp. 406-412.

Narotam, P.K., et al., "Experimental Evaluation of Collagen Sponge as a Dural Graft." *British Journal of Neurosurgery* vol. 7 (1993): pp. 635-641.

Nimni, M. E., et al., "Chemically modified collagen: A natural biomaterial for tissue replacement." *Journal of Biomedical Materials Research* vol. 21.6 (1987): pp. 741-771.

Nimni, Marcel E., "The cross-linking and structure modification of the collagen matrix in the design of cardiovascular prosthesis." *Journal of Cardiac Surgery* vol. 3.4 (1988): pp. 523-533.

O'Neill, P., et al., "Use of Porcine Dermis as Dural Substitute in 72 Patients." *Journal of Neurosurgery* vol. 61 (Aug. 1984): pp. 351-354.

Palm, S.J., et al., "Dural Closure with Nonpenetrating Clips Prevents Meningoneural Adhesions: An Experimental Study in Dogs." *Neurosurgery* vol. 45.4 (Oct. 1999):pp. 875-882.

Parizek, J., et al., "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery," *Acta Neurochir* vol. 139 (1997): pp. 827-838.

Park, Y-K., at al., "Prevention of Arachnoiditis and Postoperative Tethering of the Spinal Cord with Gore-Tex Surgical Membrane: An Experimental Study with Rats," *Neurosurgery* vol. 42.4 (Apr. 1998): pp. 813-824.

International Preliminary Report on Patentability and Written Opinion dated Feb. 17, 2009 for International Application No. PCT/US2007/074984, filed Aug. 1, 2007; all pages.

Pietrucha, K., "New Collagen Implant as Dural Substitute." *Biomaterials* vol. 12 (Apr. 1991): pp. 320-323.

Pitt, et al., "Controlled Release of Bioactive Materials"; Ed. R. Baker, New York: Academic Press, 1980.

Porchet, Francois, "Inhibition of Epidural Fibrosis with ADCON-L: Effect on Clinical Outcome One Year Following Re-operation for Recurrent Lumbar Radiculopathy." 1998, pp. 1-10.

Raul, J.S., et al., "Utilisation du Polyester Urethane (NEURO-PATCH®) Comme Substitut Dural." *Neurochirugie* vol. 49.2-3 (2003): pp. 83-89. English abstract only on p. 83.

Reddy, M., et al., "A Clinical Study of a Fibrinogen-Based Collagen Fleece for Dural Repair in Neurosurgery." *Acta Neurochirugie* vol. 144 (2002): pp. 265-269.

Riley, et al., "Percutaneous Liver Biopsy with Plugging of Needle Track: A Safe Method for Use in Patients with Impaired Coagulation." *Lancet* (Aug. 25, 1984): p. 436.

Rosenblatt, Joel, et al., "Effect of electrostatic forces on the dynamic rheological properties of injectable collagen biomaterials." *Biomaterials* vol. 13.12 (1992): pp. 878-886.

Rosenblatt, Joel, et al., "Injectable collagen as a pH-sensitive hydrogel." *Biomaterials* vol. 15.12 (1994): pp. 985-995.

Ross, Jeffrey S., et al., "Association Between Peridural Scar and Recurrent Radicular Pain After Lumbar Discectomy: Magnetic Resonance Evaluation." *Neurosurgery* (1996): pp. 855-863.

(56) References Cited

OTHER PUBLICATIONS

Rossler, B., et al., "Collagen microparticles: preparation and properties." *Journal of Microencapsulation* vol. 12.1 (Jan.-Feb. 1995): pp. 49-57.
San-Galli, F., et al., "Experimental Evaluation of a Collagen-Coated Vicryl Mesh as a Dural Substitute." *Neurosurgery* vol. 30.3 (1992): pp. 396-401.
Shaffrey, C.I., et al., "Neurosurgical Applications of Fibrin Glue: Augmentation of Dural Closure in 134 Patients." *Neurosurgery* vol. 26.2 (1990): pp. 207-210.
Sidman, et al., "Biodegradable, Implantable Sustained Release Systems Based on Glutamic Acid Copolymers." *Journal of Membrane Science* vol. 7 (1979): pp. 227-291.
Smith, K. A., et al., "Delayed Postoperative Tethering of the Cervical Spinal Cord." *Journal of Neurosurgery* vol. 81 (Aug. 1994): pp. 196-201.
Springorum, H.W., "Die Verwendung von Kollagenfolien zur Uberbruckung von Defekten des Gleitgewebes bei Achillotenotomien und Achillessehnenrupturen." *Akt. Traumata.* vol. 15 (1985): pp. 120-121. English abstract only on p. 120.
Stricker, A., et al., "Die Verwendung von TissuFoil Membran bei der Sinusbodenaugmentation." *Ellipse* vol. 17.1 (2001): pp. 1-5. English abstract only on p. 1.
Sugitachi, et al., "A Newly Devised Chemo-embolic Agent, G.T. XIII—Adm." (English abstract posted at http://www.ncbi.nlm.nih.gov/ on Jan. 3, 2001) *Gan. To. Kagaku Ryoho*. vol. 12.10 (1985): pp. 1942-1943.
Sugitachi, et al., "Locoregional Therapy in Patients with Malignant Pleural Effusion—Two Different Kinds of BAC Therapy" (English abstract posted at http://www.ncbi.nlm.nih.gov/ on Jan. 3, 2001) *Gan. To. Kagaku Ryoho*. vol. 19.10 (1992): pp. 1640-1643.
Sugitachi, et al., "Preoperative Transcatheter Arterial Chemoembolization for Locally Advanced Breast Cancer: Application for New Thrombotic Materials." *The Japanese Journal of Surgery* vol. 13.5 (1983): pp. 456-458.
TissuFleece E, Version 5, Package Leaflet, Baxter International Inc., 2003, 8 pages, English portion of instructions for use.
Tobin, et al., "Plugged Liver Biopsy in Patients with Impaired Coagulation." *Digestive Diseases and Science* vol. 34.1 (1989): pp. 13-15.
Tucker, et al., *Absorbable Gelatin (Gelfoam) Sponge*. Springfiled, Illinois: Charles T. Thomas, 1965, pp. 3-125.
Vander Salm, et al., "Reduction of Sternal Infection by Application of Topical Vancomycin." *Journal of Thoracic Surgery* vol. 98 (1989): pp. 618-622.
Vinas, F.E., et al., "Evaluation of Expanded Polytetrafluoroethylene (ePTFE) versus Polydioxanone (PDS) for the Repair of Dura Mater Defects." *Neurological Research* vol. 21 (Apr. 1999): pp. 262-268.
Wallace, D. G., et al., "Injectable cross-linked collagen with improved flow properties." *Journal of Biomedical Materials Research* vol. 23.8 (Aug. 1989): pp. 931-945.
Wallace, Donald, "The relative contribution of electrostatic interactions to stabilization of collagen fibrils." *Biopolymers* vol. 29.6-7 (May-Jun. 1990): pp. 1015-1026.
Warren, W.L., et al., "Dural Repair Using Acellular Human Dermis: Experience with 200 Cases: Technique Assessment." *Neurosurgery* vol. 46.6 (Jun. 2000): pp. 1391-1396.
Yuki, et al., "Effects of Endoscopic Variceal Sclerotherapy using GT XIII on Blood Coagulation Tests and the Renal Kallikrein-kinin System." (English abstract posted at http://www.ncbi.nlm.nih.gov/ on Jan. 3, 2001) *Gastroenterology Japan* vol. 25.5 (1990): pp. 561-567.
Ziegelaar, B.W., et al., "The characterisation of human respiratory epithelial cells cultured on reabsorbable scaffolds: first steps towards a tissue engineered tracheal replacement." *Biomaterials* vol. 23 (2002): pp. 1425-1438.
Ziegelaar, B.W., "Tissue Engineering of a Tracheal Equivalent." Doctoral Thesis at Ludwig Maximilians University, Munich, Germany, 2004, 25 pages.
Zins, et al., "US-Guided Percutaneous Liver Biopsy with Plugging of the Needle Track: A Prospective Study in 72 High-Rish Patients." *Radiology* vol. 184.3 (1992): pp. 841-843.
Office Action dated Jul. 30, 2015 for Colombia Application No. 14114385, filed May 27, 2014.

\* cited by examiner

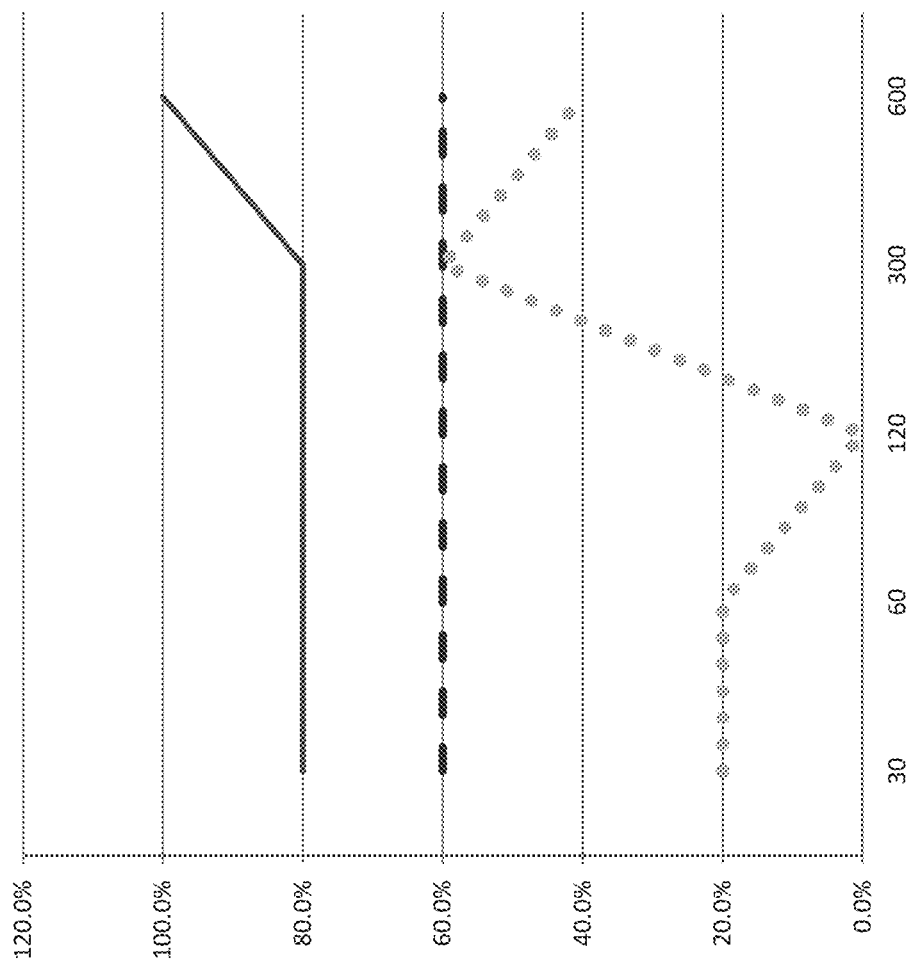

HEMOSTATIC COMPOSITIONS

CROSS-REFERENCE TO RELATED APPLICATIONS

This application is a continuation of U.S. Nonprovisional patent application Ser. No. 13/660,531, filed Oct. 25, 2012, titled "Hemostatic Compositions," which claims the benefit of U.S. Provisional Patent Application No. 61/552,270, filed Oct. 27, 2011, titled "Hemostatic Compositions," which are each incorporated herein by reference in their entirety.

FIELD OF THE INVENTION

The present invention relates to hemostatic compositions and processes for making such compositions.

BACKGROUND OF THE INVENTION

Hemostatic compositions in dry storage-stable form that comprise biocompatible, biodegradable, dry stable granular material are known e.g. from WO98/008550A or WO2003/007845A. These products have been successfully applied on the art for hemostasis. Floseal® is an example for a highly effective haemostatic agent consisting of a granular gelatin matrix swollen in a thrombin-containing solution to form a flowable paste.

Since such products have to be applied to humans, it is necessary to provide highest safety standards for quality, storage-stability and sterility of the final products and the components thereof. In addition, manufacturing and handling should be made as convenient and efficient as possible.

A successful product in this field (the Floseal® product mentioned above) utilizes a gelatin matrix used in conjugation with a reconstituted lyophilized thrombin solution. The gelatin matrix is applied as a flowable granular form of gelatin and thrombin with a gelatin content of about 11 to 14.5%. Lower gelatin content results in a runny product with diminished performance due to difficulties in having the product remain at the treatment site, especially under conditions of high blood flow. Higher gelatin particle concentration leads to a product that is difficult to deliver by usual means of administration, such as syringes or catheters, due to higher resistance to flow. The inclusion of plasticizers in the composition, e.g., polyethylene glycols, sorbitol, glycerol, and the like has been suggested (EP0927053B1) and can diminish extrusion force, but inclusion of these materials does not necessarily improve performance.

It is an object of the present invention to provide a hemostatic composition based on a crosslinked gelatin with improved adhering and hemostatic properties compared to the gelatin products such as Floseal according to the prior art and methods for making such hemostatic compositions. The compositions should also be provided in a convenient and usable manner, namely as a flowable paste usable in endoscopic surgery and microsurgery. The products must have an extrusion force of 40 N or below, preferably below 35 N, especially preferred below 20 N. The products should preferably be provided in product formats enabling a convenient provision of "ready-to-use" hemostatic compositions, which can be directly applied to an injury without any time consuming reconstitution steps.

SUMMARY OF THE INVENTION

Therefore, the present invention provides a hemostatic composition comprising crosslinked gelatin in particulate form suitable for use in hemostasis, wherein the composition is present in paste form containing 15.0 to 19.5% (w/w) crosslinked gelatin, preferably 16.0 to 19.5% (w/w), 16.5 to 19.5% (w/w), 17.0 to 18.5% (w/w) or 17.5 to 18.5% (w/w), more preferred 16.5 to 19.0% (w/w) or 16.8 to 17.8% (w/w), especially preferred 16.5 to 17.5% (w/w), and wherein the composition comprises an extrusion enhancer, especially albumin.

The invention also refers to the use of this hemostatic composition for treating an injury selected from the group consisting of a wound, a hemorrhage, damaged tissue and/or bleeding tissue comprising administering such a hemostatic composition and kits making such a hemostatic composition for the treatment of such injury.

DESCRIPTION OF SPECIFIC EMBODIMENTS OF THE INVENTION

The present invention provides a hemostatic composition comprising crosslinked gelatin in particulate form suitable for use in hemostasis, wherein the composition is present in paste form containing 15.0 to 19.5% (w/w) crosslinked gelatin (=weight of dry crosslinked gelatin per weight of final composition), preferably 16.0 to 19.5% (w/w), 16.5 to 19.5% (w/w), 17.0 to 18.5% (w/w) or 17.5 to 18.5% (w/w), more preferred 16.5 to 19.0% (w/w) or 16.8 to 17.8% (w/w), especially preferred 16.5 to 17.5% (w/w), and wherein the composition comprises an extrusion enhancer.

It has been surprisingly found within the course of the present invention that the provision of extrusion enhancers, such as albumin in the appropriate amount, enables the use of higher gelatin concentrations and that the use of higher gelatin concentrations improves the hemostatic properties of such products. This is an effect which is not suggested in the prior. Moreover, it was surprising that higher concentration of crosslinked gelatin result in better adhesive properties (in contrast to the results known in the prior art (e.g. FIG. 4 of WO2008/076407A2).

For enabling the preferred properties due to the higher gelatin concentrations in the paste according to the present invention, it is necessary to provide the extrusion enhancers in appropriate amounts. The amounts shall be high enough so as to obtain the extrusion effect, i. e. to enable a flowable paste even for amounts of 15 to 19.5% crosslinked gelatin so that the hemostatic composition can be applied e.g. in microsurgery; on the other hand, the amounts shall be as low as to prevent negative functional properties of the hemostatic composition, for example adherence to wounds or hemostatic performance. For example, if the extrusion enhancer is albumin (which is specifically preferred, especially human serum albumin), it must be provided in an amount of between 0.5 to 5.0% (w/w) (=weight of extrusion enhancer per weight of final composition), preferably 1.0 to 5.0% (w/w), preferably 2.0 to 4.5% (w/w), more preferred 1.5 to 5.0% (w/w), especially preferred about 1.5% (w/w).

Another preferred class of extrusion enhancers according to the present invention are phospholipids, such as phosphatidylcholine and -serine, or complex mixtures such as lecithins or soy bean oils.

In another preferred embodiment the present invention provides a hemostatic composition comprising crosslinked gelatin in particulate form suitable for use in hemostasis, wherein the composition is present in paste form containing 16.0 to 19.5% (w/w), preferably 16.5 to 19.5% (w/w 17.0 to 18.5% (w/w) or 17.5 to 18.5% (w/w), more preferred 16.5 to 19.0% (w/w) or 16.8 to 17.8% (w/w), especially preferred 16.5 to 17.5% (w/w), and wherein the composition comprises an extrusion enhancer. Preferably the extrusion enhancer is human serum albumin.

In another preferred embodiment the present invention provides a hemostatic composition comprising crosslinked gelatin in particulate form suitable for use in hemostasis, wherein the composition is present in paste form containing 15.0 to 19.5% (w/w) crosslinked gelatin, preferably 16.0 to 19.5% (w/w), 16.5 to 19.5% (w/w), 17.0 to 18.5% (w/w) or 17.5 to 18.5% (w/w), more preferred 16.5 to 19.0% (w/w) or 16.8 to 17.8% (w/w), especially 16.5 to 17.5% (w/w), and wherein the composition comprises an extrusion enhancer in a concentration of more than 0.8% (w/w), preferably about 3.3% (w/w). Preferably the extrusion enhancer is human serum albumin, e.g. in the above mentioned concentrations.

The hemostatic compositions according to the present invention, especially the ones that use albumin as extrusion enhancer, have specific advantages over the compositions using lower amounts of crosslinked gelatin (13 to 14.5%), especially they have an enhanced in vivo efficacy. It was unexpectedly revealed within the course of the present invention that a formulation with a higher gelatin particle concentration results in greater hemostatic performance both in ex vivo test methods that use whole human blood and in pre-clinical animal experiments. The products according to the present invention enable a reduced surgical approximation time and a faster time to hemostasis.

The compositions according to the present invention have a mean extrusion force (employing the test method described in example 1) of 40 N or below, preferably below 35 N, especially preferred below 20 N.

According to preferred embodiment of the present invention, the hemostatic composition comprises glutaraldehyde-crosslinked gelatin or genipin (Methyl (1R,2R,6S)-2-hydroxy-9-(hydroxymethyl)-3-oxabicyclo[4.3.0]nona-4,8-diene-5-carboxylate)-crosslinked gelatin, preferably type B gelatin, more preferably type B gelatin of hide origin.

Preferably, the crosslinked gelatin is present as granular material.

The hemostatic composition according to the present invention preferably comprises a gelatin polymer which is especially a type B gelatin polymer. Type B gelatin has proven to be specifically advantageous for use in hemostatic agents as the base treatment is highly effective in generating gelatin of appropriate properties and in mitigating risk of viral and zoonotic infection. A specifically preferred gelatin preparation can be prepared by processing young bovine corium with 2 N NaOH for about 1 hour at room temperature, neutralizing to pH 7-8, and heating to 70° C. The corium is then fully solubilized to gelatin with 3-10% (w/w), preferably 7-10% (w/w) gelatin in solution. This solution can be cast, dried and ground to provide gelatin type B powder.

Preferably, the gelatin has a Bloom strength of 200 to 400, especially a type B gelatin with a Bloom strength of 200 to 400. Bloom is a test to measure the strength of gelatin. The test determines the weight (in grams) needed by a probe (normally with a diameter of 0.5 inch) to deflect the surface of the gel 4 mm without breaking it. The result is expressed in Bloom (grades). To perform the Bloom test on gelatin, a 6.67% gelatin solution is kept for 17-18 hours at 10° C. prior to being tested.

The hemostatic composition according to the present invention preferably contains the crosslinked gelatin in particulate form, especially as granular material. This granular material can rapidly swell when exposed to a fluid (i.e. the diluent) and in this swollen form is capable of contributing to a flowable paste that can be applied to a bleeding site. According to a preferred embodiment, the crosslinked gelatin is provided from a dry crosslinked gelatin. This dry crosslinked gelatin powder can be prepared to re-hydrate rapidly if contacted with a pharmaceutically acceptable diluent. The gelatin granules, especially in the form of a gelatin powder, preferably comprise relatively large particles, also referred to as fragments or subunits, as described in WO98/08550A and WO2003/007845A. A preferred (median) particle size will be the range from 10 to 1.000 µm, preferably from 200 to 800 µm, but particle sizes outside of this preferred range may find use in many circumstances.

Usually, the gelatin particles have a mean particle diameter ("mean particle diameter" is the median size as measured by laser diffractometry; "median size" (or mass median particle diameter) is the particle diameter that divides the frequency distribution in half; fifty percent of the particles of a given preparation have a larger diameter, and fifty percent of the particles have a smaller diameter) from 10 to 1000 µm, preferably 50 to 700 µm, 200 to 700 µm, 300 to 550 µm, especially preferred 350 to 550 µm (median size). Although the terms powder and granular (or granulates) are sometimes used to distinguish separate classes of material, powders are defined herein as a special sub-class of granular materials. In particular, powders refer to those granular materials that have the finer grain sizes, and that therefore have a greater tendency to form clumps when flowing. Granules include coarser granular materials that do not tend to form clumps except when wet.

The present crosslinked gelatin in particulate form suitable for use in hemostasis may include dimensionally isotropic or non-isotropic forms. For example, the crosslinked gelatin in the kit according to the present invention may be granules or fibers; and may be present in discontinuous structures, for example in powder forms.

The dry gelatin composition is liquid absorbing. For example, upon contact with liquids, e.g. aqueous solutions or suspensions (especially a buffer or blood) the crosslinked gelatin takes up the liquid and will display a degree of swelling, depending on the extent of hydration. The material preferably absorbs from at least 400%, preferably about 500% to about 2000%, especially from about 500% to about 1300% water or aqueous buffer by weight, corresponding to a nominal increase in diameter or width of an individual particle of subunit in the range from e.g. approximately 50% to approximately 500%, usually from approximately 100% to approximately 250%. For example, if the (dry) granular particles have a preferred size range of 0.01 mm to 1.5 mm, especially of 0.05 mm to 1 mm, the fully hydrated composition (e.g. after administration on a wound or after contact with an aqueous buffer solution) may have a size range of 0.05 mm to 3 mm, especially of 0.25 mm to 1.5 mm.

The dry compositions will also display a significant "equilibrium swell" when exposed to an aqueous re-hydrating medium (=pharmaceutically acceptable diluent, also referred to as reconstitution medium). Preferably, the swell will be in the range from 400% to 1300%, preferably 400% to 1000%, more preferred 500% to 1100%, especially preferred from 500% to 900%, depending on its intended use. Such equilibrium swell may be controlled e.g. (for a crosslinked polymer) by varying the degree of cross-linking, which in turn is achieved by varying the cross-linking conditions, such as the duration of exposure of a cross-linking agent, concentration of a cross-linking agent, cross-linking temperature, and the like. Materials having differing equilibrium swell values perform differently in different applications. The ability to control crosslinking and equilibrium swell allows the compositions of the present invention to be optimized for a variety of uses. In addition to equilibrium swell, it is also important to control the hydration of the material immediately prior to delivery to a target site. Hydration and equilibrium swell are, of course, intimately connected. A material with 0% hydration will be non-swollen. A material with 100% hydration will be at its equilibrium water content. Hydrations between 0% and 100% will correspond to swelling between the minimum and maximum amounts. "Equilibrium swell" may be determined by subtracting the dry weight of the gelatin hydrogel powder from its weight when fully hydrated and thus fully swelled. The difference is then divided by the dry weight and multiplied by 100 to give the measure of swelling. The dry weight should be measured after exposure of the material to an elevated temperature for a time sufficient to remove substantially all residual moisture, e.g., two hours at 120° C. The equilibrium hydration of the material can be achieved by immersing the dry material in a pharmaceutically acceptable diluent, such as aqueous saline, for a time period sufficient for the water content to become constant, typically for from 18 to 24 hours at room temperature.

The crosslinked gelatin may be provided as a film which can then be milled to form a granular material. Most of the particles contained in a granular material (e.g. more than 90% w/w) have preferably particle sizes of 10 to 1.000 μm, preferably 50 to 700 μm, 200 to 700 μm, 300 to 550 μm, especially preferred 350 to 550 μm.

Preferably, the flowable form of the hemostatic composition contains particles that are more than 50% (w/w) with a size of 100 to 1000 μm, preferably more than 80% (w/w) with a size of 100 to 1000 μm.

Examples of suitable gelatin materials for crosslinking are described i.a. in examples 1 and 2 of EP1803417B1 and example 14 of U.S. Pat. No. 6,066,325A and U.S. Pat. No. 6,063,061A. Gelatin may also be used with processing aids, such as PVP, PEG and/or dextran as re-hydration aids.

In one particular aspect of the present invention, compositions will comprise crosslinked gelatin powders having a moisture content of 20% (w/w) or less, wherein the powder was crosslinked in the presence of a re-hydration aid so that the powder has an aqueous re-hydration rate which is at least 5% higher than the re-hydration rate of a similar powder prepared without the re-hydration aid. The "re-hydration rate" is defined according to EP1803417B1 to mean the quantity of an aqueous solution, typically 0.9% (w/w) saline that is absorbed by a gram of the powder (dry weight basis) within thirty seconds, expressed as g/g. The rehydration rate is measured by mixing the crosslinked gelatin with saline solution for 30 seconds and depositing the wet gelatin on a filter membrane under vacuum to remove the free aqueous solution. One then records the weight of the wet gelatin retained on the filter, dries it (e.g. 2 hr at 120° C.), then records the dry weight of the gelatin and calculates the weight of solution that was absorbed per gram of dry gelatin.

Preferred compositions of the present invention will have a re-hydration rate of at least 3 g/g, preferably at least 3.5 g/g, and often 3.75 g/g or higher. Re-hydration rates of similar powders prepared without the re-hydration aids are typically below three, and a percentage increase in re-hydration rate will usually be at least 5%, preferably being at least 10%, and more preferably being at least 25% or higher.

Crosslinking can be done with any suitable crosslinker, e.g. glutaraldehyde such as e.g. described in WO98/08550A and WO2003/007845A. Crosslinking can also be carried out with a non-toxic crosslinker such as genipin and the like.

Production cost is less for a genipin crosslinked gelatin product according to the present invention than a glutaraldehyde crosslinked one, since reagent, energy, and time costs are lower. The genipin crosslinked gelatin reaction can be performed in water at neutral pH at room temperature for ≤16 hours. The product can be cleaned-up by an ethanol and/or water wash which is not only cheaper, but more importantly, safer for the operator.

The method preferably applies the gelatin as being present in dry form before the crosslinking step.

The preferred genipin-type crosslinker according to the present invention is, of course, genipin (Methyl (1R,2R,6S)-2-hydroxy-9-(hydroxymethyl)-3-oxabicyclo[4.3.0]nona-4,8-diene-5-carboxylate); however, also other crosslinkers of the iridoid- or secoiridoid-type may be used, such as oleuropein. Preferred concentrations of genipin for crosslinking are in the range of 0.5 to 20 mM, preferably 1 to 15 mM, especially 2 to 10 mM.

According to a preferred embodiment of the present invention, the genipin crosslinked gelatin is subjected to a quenching/oxidation step with oxidizing agents such as bleach, tBu-hydroperoxide, etc., preferably to a treatment with sodium percarbonate, sodium hypochlorite, chlorine water or hydrogen peroxide ($H_2O_2$), especially preferred is a treatment with sodium percarbonate or $H_2O_2$ most preferred is a treatment with percarbonate.

Preferred $H_2O_2$ concentrations are 0.5 to 20% (w/w), especially 1 to 15% (w/w), more preferred about 5% (w/w). In an especially preferred embodiment the genipin concentration is between 5 to 10 mM, the reaction time of gelatin with genipin is between 3 to 10 hours, especially 6 hours, the $H_2O_2$ concentration is between 3 to 5% (w/w) and the reaction time of the genipin-crosslinked gelatin with $H_2O_2$ is about 20 hours, Preferred percarbonate concentrations are between 1 to 10% (w/w), especially 1 to 5% (w/w), more preferred 1 to 4% (w/w). In an especially preferred embodiment the genipin concentration is between 5 to 10 mM (especially about 8 nM), the reaction time of gelatin with genipin is between 3 to 10 hours (especially about 5 hours), the percarbonate concentration is between 1 to 10% (w/w), especially preferred between 1 to 4% w/w, and the reaction time of the genipin-crosslinked gelatin with percarbonate is between 1 to 20 hours, preferably between 1 to 5 hours (e.g. 1, 2 or 3 hours).

Quenching may also be carried out in presence of antioxidants such as sodium ascorbate or by controlling oxidation potential of the reaction environment such as carrying out quenching and/or genipin reaction in an inert atmosphere such as nitrogen or argon.

Preferred crosslinking reaction conditions include the performance in aqueous solution, preferably in a phosphate buffered saline (PBS)/ethanol buffer, especially at a pH of 4 to 12, preferably of 5.0 to 10.0, especially of 6 to 8, or in deionized water or other aqueous buffers which may contain between 0 to 50% of a water miscible organic solvent. A PBS buffer contains physiological amounts of NaCl and KCl in a phosphate buffer at a physiological pH. An example for a PBS buffer contains 137 mM NaCl, 2.7 mM KCl, 10 mM $Na_2HPO_4 \cdot 2H_2O$, 1.76 mM $KH_2PO_4$ (pH=7.4). Another example of a PBS buffer consists of 137 mM NaCl, 2.7 mM KCl, 4.3 mM $Na_2HPO_4$ and 1.4 mM $KH_2PO_4$ (pH=7.5).

The reaction may also be carried out in an aqueous buffer containing up to 50% of a water-miscible organic solvent and/or processing aids such as PEG, PVP, mannitol, sodium percarbonate, sodium lactate, sodium citrate, sodium ascorbate etc.

Preferably, the crosslinking step is performed at a temperature of 4° C. to 45° C., preferably of 15 to 45° C., especially of 20 to 40° C.

The crosslinking step may be followed by a quenching step, especially with an amino-group containing quencher, preferably an amino acid, especially glycine. With the quencher, yet unreacted genipin-type crosslinkers are inactivated (e.g. by reaction with the quencher in excess) to prevent further crosslinking. Quenching may also be carried out by raising pH of solution to between 8 to 14, or by using nucleophilic compounds containing amino, thiol, or hydroxyl groups and also a combination of pH raising and using nucelophilic compounds. The quenching step after the genipin-gelatin crosslinking reaction according to the present invention can be actively directed to impart desired physical performance such as swell and TEG which are important determinants of hemostatic activity above and beyond the general genipin-crosslinking alone.

The crosslinked gelatin is preferably washed after the crosslinking step, preferably by methanol, ethanol or water, especially by deionized water. Another preferred washing step applies an aqueous buffer containing up to 50% (v/v) of water-miscible organic solvent and/or one or more processing aids.

According to a preferred embodiment, the crosslinked gelatin is dried. In such a dried state, the hemostatic composition is storage-stable for long time even at elevated temperatures (e.g. more than 20° C., more than 30° C. or even more than 40° C.). Preferred dryness conditions include crosslinked biocompatible polymers which are dried to have a moisture content of below 15% (w/w), preferably below 10%, more preferred below 5%, especially below 1%. In another preferred embodiment the product may be supplied in a hydrated or wet state where the hydrating solution may be a biocompatible buffer or solution.

A Glu-Gel product has a tendency to be camouflaged by surrounding tissue, since it's slightly yellow color blends in with it. This makes visual evaluation of the desired application problematic. The genipin crosslinked gelatin products according to the present invention appear variable color from pale yellow to dark blue or green based upon degree of crosslinking reaction conditions, and subsequent processing and finishing steps. This tunability of color and ability to obtain desired color in finished product color has the added advantage of providing physicians visual indication of proper product application in wound sites, since this color differentiates it from surrounding tissue, instead of potentially being camouflaged by it. This is another novel feature of this invention. On the other hand, the color can be removed to obtain a non-colored product, depending on the needs with respect to the final products.

In a preferred embodiment the biocompatible polymer, e.g. gelatin, crosslinked with a genipin-type crosslinker, e.g. genipin, is a homogeneously (uniformly) crosslinked polymer as can be shown e.g. by fluorescence measurements as described in Example 3 of the present application. In an especially preferred embodiment the biocompatible polymer, such as gelatin, is present as a homogeneously genipin crosslinked biocompatible polymer, such as gelatin, in particulate form.

A hemostatic composition according to the present invention is preferred, wherein excipients, such as lubricants, e.g. hyaluronic acid, are present.
In another embodiment of the present invention excipients, such as lubricants, e.g. hyaluronic acid, are excluded.

The pharmaceutically acceptable diluent is preferably an aqueous solution and may contain a substance selected from the group consisting of NaCl, $CaCl_2$ and sodium acetate. For example, a pharmaceutically acceptable diluent comprises water for injection, and—independently of each other—50 to 200 mM NaCl (preferably 150 mM), 10 to 80 mM $CaCl_2$ (preferably 40 mM) and 1 to 50 mM sodium acetate (preferably 20 mM). In another embodiment the pharmaceutically acceptable diluent contains less than 35 g/l of mannitol, preferably less than 25 g/l, more preferred less than 10 g/l, especially preferred the pharmaceutically acceptable diluent is essentially free of mannitol.

According to a preferred embodiment, the pharmaceutically acceptable diluent comprises thrombin, preferably 10 to 1000 I.U. thrombin/ml, especially 250 to 700 I.U. thrombin/ml. Preferably, the hemostatic composition in this ready to use form contains 10 to 100.000 International Units (I.U.) of thrombin, more preferred 100 to 10.000 I.U., especially 500 to 5.000 I.U. Thrombin (or any other coagulation inducing agent, such as snake venom, a platelet activator, a thrombin receptor activating peptide and a fibrinogen precipitating agent) can be derived from any thrombin preparation which is suitable for use in humans (i.e. pharmaceutically acceptable). Suitable sources of thrombin include human and bovine blood, plasma or serum (thrombin of other animal sources can be applied if no adverse immune reactions are anticipated), thrombin of recombinant origin (e.g. human recombinant thrombin) and autologous human thrombin can be preferred for some applications.

The pharmaceutically acceptable diluent is used in an amount to achieve the desired end-concentration in the ready-to-use composition. The thrombin preparation may contain other useful component, such as ions, buffers, excipients, stabilizers, etc. Preferably, the thrombin preparation contains human albumin as the extrusion enhancer. Preferred salts are NaCl and/or $CaCl_2$, both used in the usual amounts and concentrations applied for thrombin (e.g. 0.5 to 1.5% NaCl (e.g. 0.9%) and/or 20 to 80 mM $CaCl_2$ (e.g. 40 mM)).

In a further embodiment, the diluent can also include a buffer or buffer system so as to buffer the pH of the reconstituted dry composition, preferably at a pH of 3.0 to 10.0, more preferred of 6.4 to 7.5, especially at a pH of 6.9 to 7.1.

Establishment of appropriate amounts of crosslinked gelatin, diluent and extrusion enhancer may be made in the kit according to the aforementioned prerequisites: For example a) a vial with 0.736 to 0,995 g dry crosslinked gelatin (corresponding to 15.0 to 19.5% (w/w) in the final product) may be provided and b) a second vial with 4 ml diluent with 60 to 240 mg albumin and, optionally, thrombin at a concentration of 500 I.U./ml and/or 40 mM $CaCl_2$. Alternatively, albumin may be added in lyophilized form to the dry gelatin component a) of the kit. For example, a) a vial with 0.573 to 0.775 g dry crosslinked gelatin (corresponding to 15.0 to 19.5% (w/w) in the final product) thereof 48 to 192 mg albumin may be provided and b) a second vial with 3.2 ml diluent and, optionally, thrombin at a concentration of 500 I.U./ml and/or 40 mM $CaCl_2$.

The crosslinked gelatin component of the kit according to the present invention is preferably provided as a dry composition, wherein the crosslinked gelatin is present in dry form.

A substantially dry crosslinked gelatin composition according to the present invention has a residual content of moisture which may approximately correspond to the moisture content of comparable available products, such as Floseal® (Floseal, for example, has approximately 8-12% moisture as a dry product).

The dry crosslinked gelatin in particulate form suitable for use in hemostasis in the kit according to the present invention is preferably gelatin in powder form, especially wherein the powder particles have a median particle size of 10 to 1000 μm, preferably 50 to 700 μm, 200 to 700 μm, 300 to 550 μm, especially preferred 350 to 550 μm. A "dry granular preparation of crosslinked gelatin" according to the present invention is in principle known e.g. from WO98/08550A. Preferably, the crosslinked gelatin is a biocompatible, biodegradable dry stable granular material.

According to another aspect, the present invention relates to a hemostatic composition according to the present invention for use in the treatment of an injury selected from the group consisting of a wound, a hemorrhage, damaged tissue, bleeding tissue and/or bone defects.

Another aspect of the present invention is a method of treating an injury selected from the group consisting of a wound, a hemorrhage, damaged tissue and/or bleeding tissue comprising administering a hemostatic composition according to the present invention to the site of injury.

According to another aspect, the present invention also provides a method for delivering a hemostatic composition according to the invention to a target site in a patient's body, said method comprising delivering a hemostatic composition produced by the process according to the present invention to the target site. Although also the dry composition can be directly applied to the target site (and, optionally be contacted with a diluent at the target site, if necessary), it is preferred to contact the dry hemostatic composition with a pharmaceutically acceptable diluent before administration to the target site, so as to obtain a hemostatic composition according to the present invention in paste form.

In such a method, a kit for making a flowable paste of crosslinked gelatin for the treatment of an injury selected from the group consisting of a wound, a hemorrhage, damaged tissue and/or bleeding tissue, may be applied, this kit comprising
a) a dry hemostatic composition comprising crosslinked gelatin in particulate form to be reconstituted to a flowable paste containing 15.0 to 19.5% (w/w) crosslinked gelatin (=weight of dry gelatin to weight of final composition), preferably 16.0 to 19.5% (w/w), 16.5 to 19.5% (w/w), 17.0 to 18.5% (w/w) or 17.5 to 18.5% (w/w), more preferred 16.5 to 19.0% (w/w) or 16.8 to 17.8% (w/w), especially preferred 16.5 to 17.5% (w/w), crosslinked gelatin and
b) a pharmaceutically acceptable diluent for reconstitution of the hemostatic composition, wherein either the composition or the diluent comprises an extrusion enhancer, especially albumin, in a suitable amount, for example (for albumin) in an amount which leads to an albumin concentration in the reconstituted paste of between 0.5 to 5.0% (w/w) (=weight of extrusion enhancer per weight of final composition), preferably 1.0 to 5.0% (w/w), preferably 2.0 to 4.5% (w/w), more preferred 1.5 to 5.0% (w/w), especially preferred about 1.5% (w/w).

A preferred further component of such a kit is—specifically if the hemostatic composition is contained in dry form—a diluent for reconstitution (=re-hydration medium) of the hemostatic composition. Further components of the kit may be administration means, such as syringes, catheters, brushes, etc. (if the compositions are not already provided in the administration means) or other components necessary for use in medical (surgical) practice, such as substitute needles or catheters, extra vials or further wound cover means. Preferably, the kit according to the present invention comprises a syringe housing the dry and stable hemostatic composition and a syringe containing the diluent (or provided to take up the diluent from another diluent container).

In a preferred embodiment, the pharmaceutically acceptable diluent is provided in a separate container. This can preferably be a syringe. The diluent in the syringe can then easily be applied to the final container for reconstitution of the dry hemostatic compositions according to the present invention. If the final container is also a syringe, both syringes can be finished together in a pack. It is therefore preferred to provide the dry hemostatic compositions according to the present invention in a syringe which is finished with a diluent syringe with a pharmaceutically acceptable diluent for reconstituting said dry and stable hemostatic composition.

According to a preferred embodiment, the final container further contains an amount of a stabilizer effective to inhibit modification of the polymer when exposed to the sterilizing radiation, preferably ascorbic acid, sodium ascorbate, other salts of ascorbic acid, or an antioxidant.

With such a pharmaceutically acceptable diluent, a ready to use form of the present hemostatic composition may be provided which can then be directly applied to the patient. Accordingly, also method for providing a ready to use form of a hemostatic composition according to the present invention is provided, wherein the hemostatic composition is provided in a first syringe and a diluent for reconstitution is provided in a second syringe, the first and the second syringe are connected to each other, and the fluid is brought into the first syringe to produce a flowable form of the hemostatic composition; and optionally returning the flowable form of the hemostatic composition to the second syringe at least once. Preferably, the ready-to use preparations are present or provided as hydrogels. Products of this kind are known in principle in the art, yet in a different format. Therefore, a method for providing a ready to use form of a hemostatic composition according to the present invention, wherein the hemostatic composition is provided in a first syringe and a diluent for reconstitution is provided in a second syringe, the first and the second syringe are connected to each other, and the diluent is brought into the first syringe to produce a flowable form of the hemostatic composition; and optionally returning the flowable form of the hemostatic composition to the second syringe at least once, is a preferred embodiment of the present invention. This process (also referred to as "swooshing") provides a suitable ready-to-use form of the compositions according to the present invention which can easily and efficiently be made also within short times, e.g. in emergency situations during surgery. This flowable form of the hemostatic composition provided by such a method is specifically suitable for use in the treatment of an injury selected from the group consisting of a wound, a hemorrhage, damaged tissue, bleeding tissue and/or bone defects.

For stability reasons, such products (as well as the products according to the present invention) are usually provided in a dry form in a final container and brought into the ready-to-use form (which is usually in the form of a (hydro) gel, suspension or solution) immediately before use, necessitating the addition of a pharmaceutically acceptable diluents (=re-hydration medium).

According to another aspect, the present invention relates to a method for providing a ready to use form of a hemostatic composition according to the present invention, wherein the hemostatic composition is provided in a first syringe and a diluent for reconstitution is provided in a second syringe, the first and the second syringe are connected to each other, and the fluid is brought into the first syringe to produce a flowable form of the hemostatic composition; and optionally returning the flowable form of the hemostatic composition to the second syringe at least once.

Preferably, the flowable form of the hemostatic composition according to the present invention contains more than 50% (w/w) particles with a size of 100 to 1000 µm, preferably more than 80% (w/w) particles with a size of 100 to 1000 µm.

The biocompatible hemostatic crosslinked polymer according to the present invention—once applied to a wound—forms an efficient matrix which can form a barrier for blood flow. Specifically the swelling properties of the hemostatic polymer can make it an effective mechanical barrier against bleeding and re-bleeding processes.

The present composition may additionally contain a hydrophilic polymeric component (also referred to as "reactive hydrophilic component" or "hydrophilic (polymeric) crosslinker") which further enhances the adhesive properties of the present composition. This hydrophilic polymeric component of the haemostatic composition according to the present invention acts as a hydrophilic crosslinker which is able to react with its reactive groups once the haemostatic composition is applied to a patient (e.g. to a wound of a patient or another place where the patient is in need of a hemostatic activity). Therefore it is important for the present invention that the reactive groups of the hydrophilic polymeric component are reactive when applied to the patient. It is therefore necessary to manufacture the haemostatic composition according to the present invention so that the reactive groups of the polymeric component which should react once they are applied to a wound are retained during the manufacturing process.

For hydrophilic polymeric crosslinkers whose reactive groups are hydrolysable, premature contact with water or aqueous liquids has to be prevented before administration of the haemostatic composition to the patient, especially during manufacture. However, processing of the hydrophilic polymeric component during manufacturing may be possible also in an aqueous medium at conditions where the reactions of the reactive groups are inhibited (e.g. at a low pH). If the hydrophilic polymeric components can be melted, the melted hydrophilic polymeric components can be sprayed or printed onto the matrix of crosslinked gelatin. It is also possible to mix a dry form (e.g. a powder) of the hydrophilic polymeric component with a dry form of the crosslinked gelatin. If necessary, then an increase of the temperature can be applied to melt the sprinkled hydrophilic polymeric component to the crosslinked gelatin to achieve a permanent coating of the haemostatic composition. Alternatively, these hydrophilic polymeric components can be taken up into inert organic solvents (inert vis-à-vis the reactive groups of the hydrophilic polymeric components) and brought onto the matrix of the crosslinked gelatin. Examples of such organic solvents are dry ethanol, dry acetone or dry dichloromethane (which are e.g. inert for hydrophilic polymeric components, such as NHS-ester substituted PEGs). Alternatively, nucleophilic groups may also be added (e.g. PEG-SH).

In a preferred embodiment the hydrophilic polymer component is a single hydrophilic polymer component and is a polyalkylene oxide polymer, preferably a PEG comprising polymer. The reactive groups of this reactive polymer are preferably electrophilic groups.

The reactive hydrophilic component may be a multi-electrophilic polyalkylene oxide polymer, e.g. a multi-electrophilic PEG. The reactive hydrophilic component can include two or more electrophilic groups, preferably a PEG comprising two or more reactive groups selected from succinimidylesters ($-CON(COCH_2)_2$), aldehydes ($-CHO$) and isocyanates ($-N=C=O$), e.g. a component as disclosed in the WO2008/016983 A (incorporated herein by reference in its entirety).

Preferred electrophilic groups of the hydrophilic polymeric crosslinker according to the present invention are groups reactive to the amino-, carboxy-, thiol- and hydroxy-groups of proteins, or mixtures thereof.

Preferred amino group-specific reactive groups are NHS-ester groups, imidoester groups, aldehyde-groups, carboxy-groups in the presence of carbodiimides, isocyanates, or THPP (beta-[Tris(hydroxymethyl)phosphino]propionic acid), especially preferred is Pentaerythritolpoly(ethyleneglycol)ether tetrasuccinimidyl glutarate (=Pentaerythritol tetrakis[1-1'-oxo-5'-succinimidylpentanoate-2-poly-oxoethyleneglycole]ether (=an NHS-PEG with MW 10,000).

Preferred carboxy-group specific reactive groups are amino-groups in the presence of carbodiimides.

Preferred thiol group-specific reactive groups are maleimides or haloacetyls.

Preferred hydroxy group-specific reactive group is the isocyanate group.

The reactive groups on the hydrophilic cross-linker may be identical (homo-functional) or different (hetero-functional). The hydrophilic polymeric component can have two reactive groups (homo-bifunctional or hetero-bifunctional) or more (homo/hetero-trifunctional or more).

In special embodiments the material is a synthetic polymer, preferably comprising PEG. The polymer can be a derivative of PEG comprising active side groups suitable for cross-linking and adherence to a tissue.

By the reactive groups the hydrophilic reactive polymer has the ability to cross-link blood proteins and also tissue surface proteins. Cross-linking to the crosslinked gelatin is also possible.

The multi-electrophilic polyalkylene oxide may include two or more succinimidyl groups. The multi-electrophilic polyalkylene oxide may include two or more maleimidyl groups.

Preferably, the multi-electrophilic polyalkylene oxide is a polyethylene glycol or a derivative thereof.

In a most preferred embodiment the hydrophilic polymeric component is pentaerythritolpoly(ethyleneglycol)ether tetrasuccinimidyl glutarate (=COH102, also pentaerythritol tetrakis[1-1'-oxo-5'-succinimidylpentanoate-2-poly-oxoethyleneglycole]ether).

The hydrophilic polymeric component is a hydrophilic crosslinker. According to a preferred embodiment, this crosslinker has more than two reactive groups for crosslinking ("arms"), for example three, four, five, six, seven, eight, or more arms with reactive groups for crosslinking. For example, NHS-PEG-NHS is an effective hydrophilic crosslinker according to the present invention. However, for some embodiments, a 4-arm polymer (e.g. 4-arms-p-NP-PEG) may be more preferred; based on the same rationale, an 8-arm polymer (e.g. 8-arms-NHS-PEG) may even be more preferred for those embodiments where multi-reactive cross-linking is beneficial. Moreover, the hydrophilic crosslinker is a polymer, i.e. a large molecule (macromolecule) composed of repeating structural units which are typically connected by covalent chemical bonds. The hydrophilic polymer component should have a molecular weight of at least 1000 Da (to properly serve as crosslinker in the hemostatic composition according to the present invention); preferably the crosslinking polymers according to the present invention has a molecular weight of at least 5000 Da, especially of at least 8000 Da.

For some hydrophilic crosslinkers, the presence of basic reaction conditions (e.g. at the administration site) is preferred or necessary for functional performance (e.g. for a faster cross-linking reaction at the administration site). For example, carbonate or bicarbonate ions (e.g. as a buffer with a pH of 7.6 or above, preferably of 8.0 or above, especially of 8.3 and above) may be additionally provided at the site of administration (e.g. as a buffer solution or as a fabric or pad soaked with such a buffer), so as to allow an improved performance of the hemostatic composition according to the present invention or to allow efficient use as a hemostatic and/or wound adherent material.

The reactivity of the hydrophilic polymeric component (which, as mentioned, acts as a crosslinker) in the composition according to the present invention is retained in the composition. This means that the reactive groups of the crosslinker have not yet reacted with the haemostatic composition and are not hydrolyzed by water (or at least not in a significant amount which has negative consequences on the hemostatic functionality of the present compositions). This can be achieved by combining the crosslinked gelatin with the hydrophilic crosslinker in a way which does not lead to reaction of the reactive groups of the crosslinker with the hemostatic polymer or with water. Usually, this includes the omitting of aqueous conditions (or wetting), especially wetting without the presence of acidic conditions (if crosslinkers are not reactive under acidic conditions). This allows the provision of reactive haemostatic materials.

Preferred ratios of the crosslinked gelatin to hydrophilic polymeric component in the hemostatic composition according to the present invention are from 0.1 to 50% (w/w), preferably from 5 to 40% (w/w).

Further components may be present in the hemostatic composition according to the present invention. According to preferred embodiments, the hemostatic compositions according to the present invention may further comprise a substance selected from the group consisting of antifibrinolytic, procoagulant, platelet activator, antibiotic, vasoconstrictor, dye, growth factors, bone morphogenetic proteins and pain killers.

The present invention also refers to a finished final container containing the hemostatic composition according to the present invention. This finished container contains the hemostatic composition according to the present invention in a sterile, storage-stable and marketable form. The final container can be any container suitable for housing (and storing) pharmaceutically administrable compounds. Syringes, vials, tubes, etc. can be used; however, providing the hemostatic compositions according to the present invention in a syringe is specifically preferred. Syringes have been a preferred administration means for hemostatic compositions as disclosed in the prior art also because of the handling advantages of syringes in medical practice. The compositions may then preferably be applied (after reconstitution) via specific needles of the syringe or via suitable catheters. The reconstituted hemostatic compositions (which are preferably reconstituted to form a hydrogel) may also be applied by various other means e.g. by a spatula, a brush, a spray, manually by pressure, or by any other conventional technique. Administration of the reconstituted hemostatic composition to a patient by endoscopic (laparoscopic) means is specifically preferred. Usually, the reconstituted hemostatic compositions according to the present invention will be applied using a syringe or similar applicator capable of extruding the reconstituted composition through an orifice, aperture, needle, tube, or other passage to form a bead, layer, or similar portion of material. Mechanical disruption of the compositions can be performed by extrusion through an orifice in the syringe or other applicator, typically having a size in the range from 0.01 mm to 5.0 mm, preferably 0.5 mm to 2.5 mm. Preferably, however, the hemostatic composition will be initially prepared from a dry form having a desired particle size (which upon reconstitution, especially by hydration, yields subunits of the requisite size (e.g. hydrogel subunits)) or will be partially or entirely mechanically disrupted to the requisite size prior to a final extrusion or other application step. It is, of course evident, that these mechanical components have to be provided in sterile form (inside and outside) in order to fulfill safety requirements for human use.

The hemostatic composition according to the present invention is preferably applied in its pasty form to a patient from a container as described in Example 1 with an extrusion force of 40 N or lower, such as lower 30N or lower 20N, preferably in a range of 15 to 30 N.

Another aspect of the invention concerns a method for providing a ready-to-use hemostatic composition comprising contacting a hemostatic composition according to the present invention.

The invention is further described in the examples below and the drawing figures, yet without being restricted thereto.

FIG. 1 shows the mean extrusion force of glutaraldehyde crosslinked gelatin pastes containing 17.5% (w/w) crosslinked gelatin with various concentrations of human serum albumin in the thrombin component (extrusion force needed to push product out of syringe at compression speed 250 mm/min, calculated at 35 mm distance; all products incubated for 30 minutes at room temperature, quick re-swooshing shortly before extrusion force measurement). The x-axis shows the human serum albumin concentration in the thrombin component in [g/l], the y-axis shows the mean extrusion force in [N].

Figure 5:
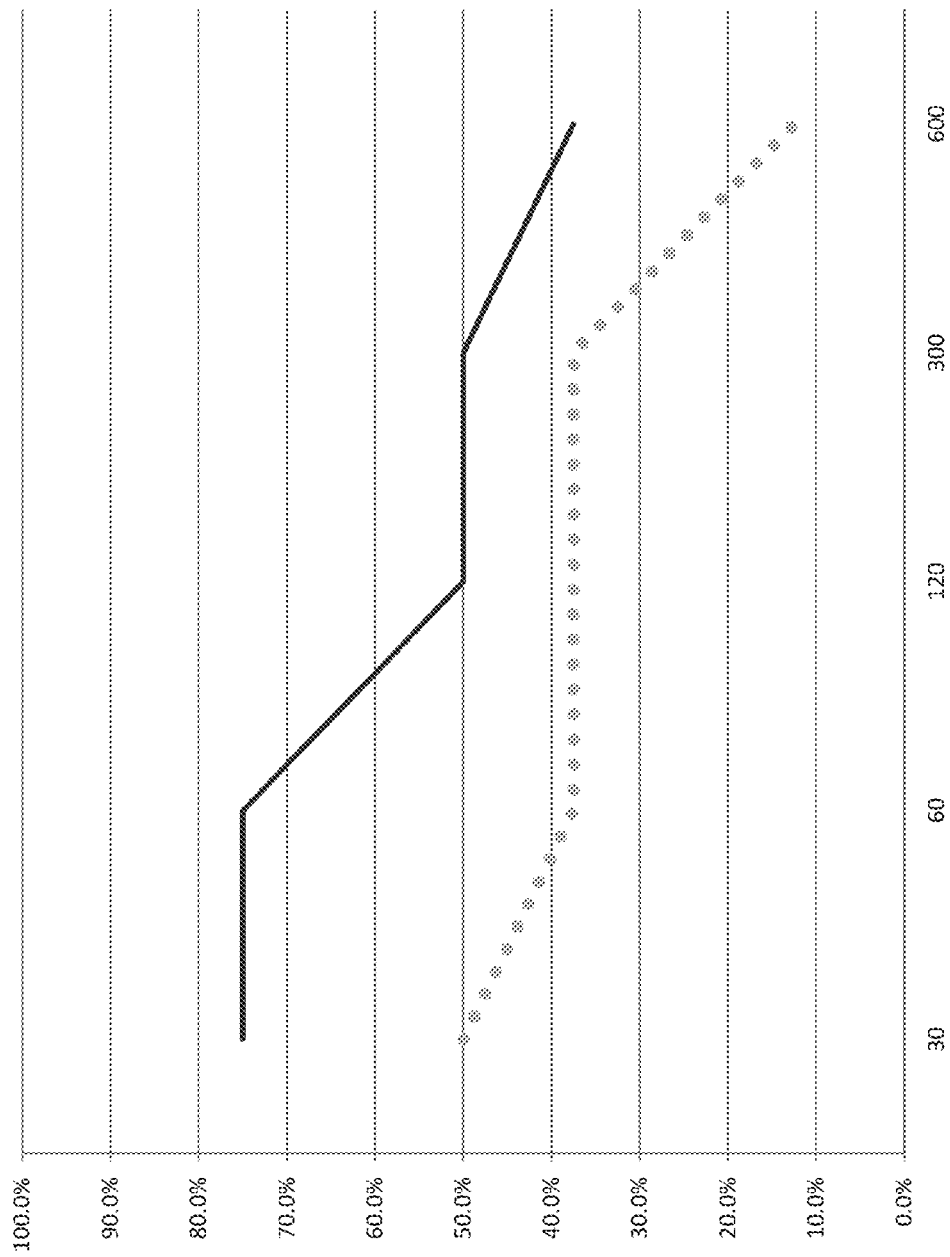
Figure 6:
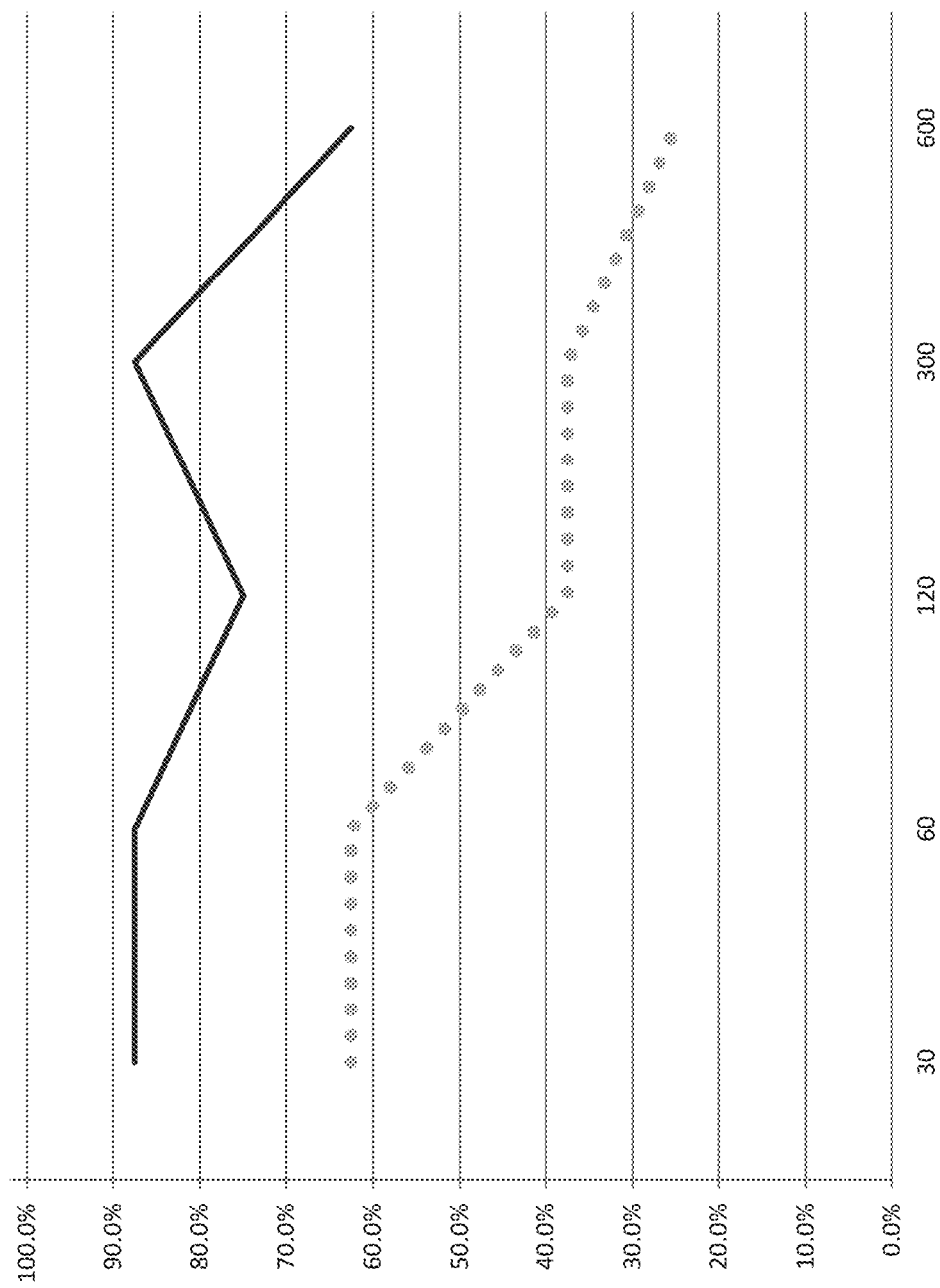
Figure 7:
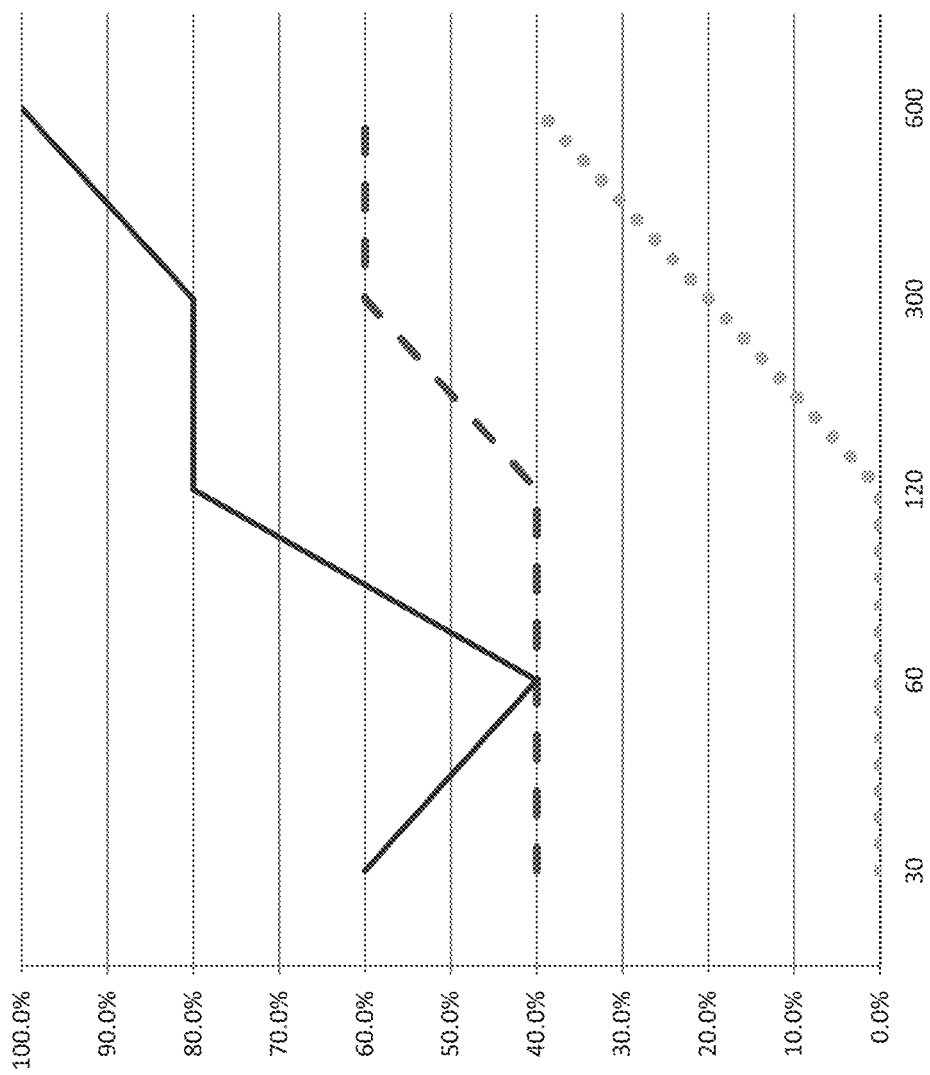

FIGS. 5 to 8 show the hemostatic efficacy in Porcine Liver Punch-Biopsy Model of different preparations. The x-axis shows the time after application in [seconds], the y-axis shows percent of hemostatic success (defined as "no bleeding" in FIG. 5 and as "no bleeding" or "ooze" in FIG. 6). In FIGS. 5 and 6 the symbols mean:
——— glutaraldehyde crosslinked gelatin with 50 g/l human serum albumin in the thrombin solution (n=8)
-------- glutaraldehyde crosslinked gelatin with 75 g/l human serum albumin in the thrombin solution (n=8)
In FIGS. 7 and 8 the symbols mean:
——— ≈17.5% (w/w) glutaraldehyde crosslinked gelatin
-------- ≈14.5% (w/w) glutaraldehyde crosslinked gelatin
········ ≈17.5% (w/w) glutaraldehyde crosslinked gelatin plus 2.5% PEG10.000 in thrombin solution

EXAMPLES

Example 1: Determination of Extrusion Force (EF)

An Instron model 5544 mechanical tester equipped with a 100 N load cell operating at a cross-beam speed of 250 mm/min was used to measure extrusion forces needed to extrude the product from a syringe. The necessary extrusion forces were measured during the complete cross-beam displacement (34 mm deflection) which corresponds to a distance a syringe plunger moves in order to extrude almost the entire product out of the syringe. From these forces the mean extrusion forces were calculated as follows:

$$\text{Total} \frac{\text{Energy (mJ)}}{\text{Max. Deflection (mm)}} = \text{Mean Force}(N)$$

Samples for this test were prepared as follows: A 5 ml standard syringe (with a cylindric body having an inner diameter of 12.2 mm) with a male luer lock system (the inner nozzle lumen diameter where the adapter is attached measures 2.54 mm) is filled with 0.704 g dry mass of the solid sample (approx. 0.8 g taking the residual moisture of approx. 12% into account). As a diluent 3.2 ml of a thrombin solution containing 500 IU/ml thrombin in 40 mM calcium chloride and either 0, 5, 15, 25, 50 or 75 mg/ml human serum albumin was used. The diluent and the solid component were mixed by connecting the syringe holding the diluent (a standard 5 ml syringe with a female luer lock system) and the syringe holding the dry component and pushing the contents back and forth at least 10 times (this mixing technique is called "swooshing"). Thereafter the sample was incubated for 30 min at room temperature before measurement. After incubation each sample was "re-swooshed" two times and the syringe holding the product (the syringe that previously held the dry component as mentioned above) was connected to a malleable applicator (female luer connector system, inner tube diameter of 2.29 mm holding two wires and having a total length of 141.5 mm). The syringe was assembled to the applicator and placed into the Instron set up and the test was started.

The syringes and the applicator were commercially available as parts of the Floseal Hemostatic Matrix product from Baxter.

Figure 1:
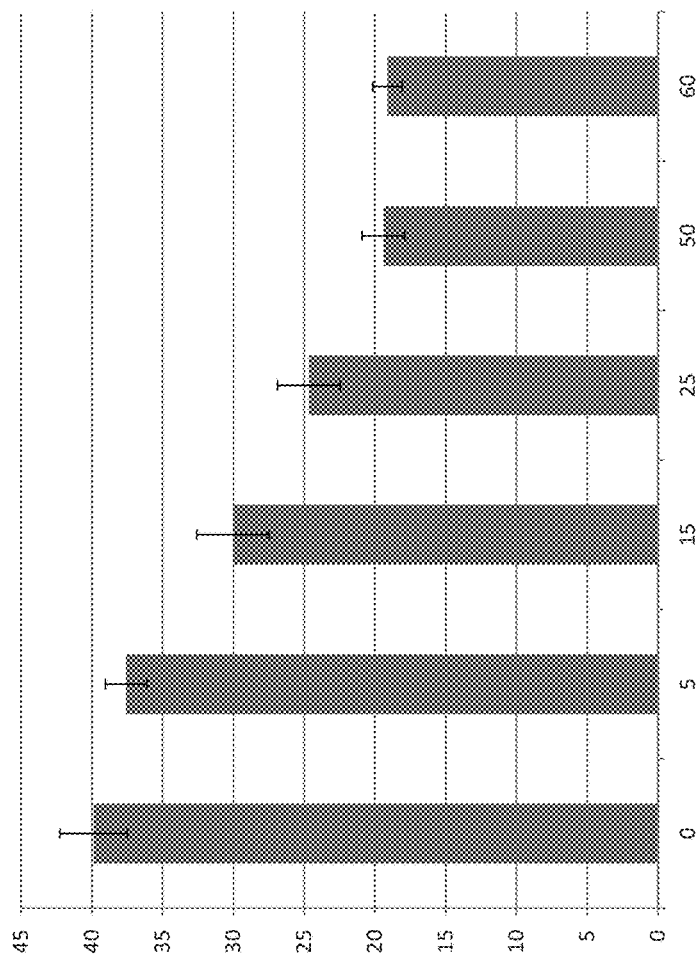
Figure 2:
FIG. 2 shows the consistency of crosslinked gelatin pastes containing 17.5% (w/w) crosslinked gelatin depending on the concentration of human serum albumin.
Figure 2:
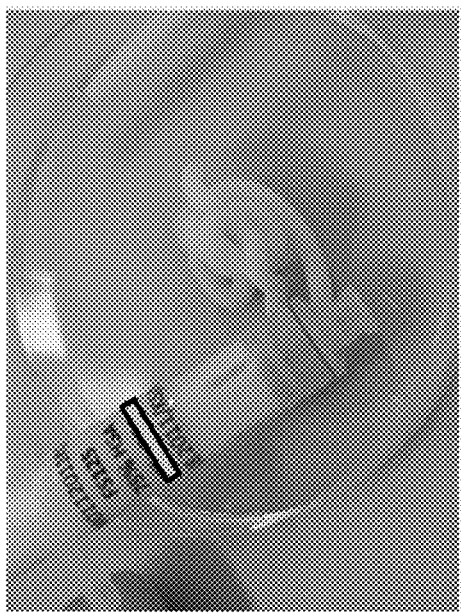
Figure 2:
Figure 2:
Figure 3:
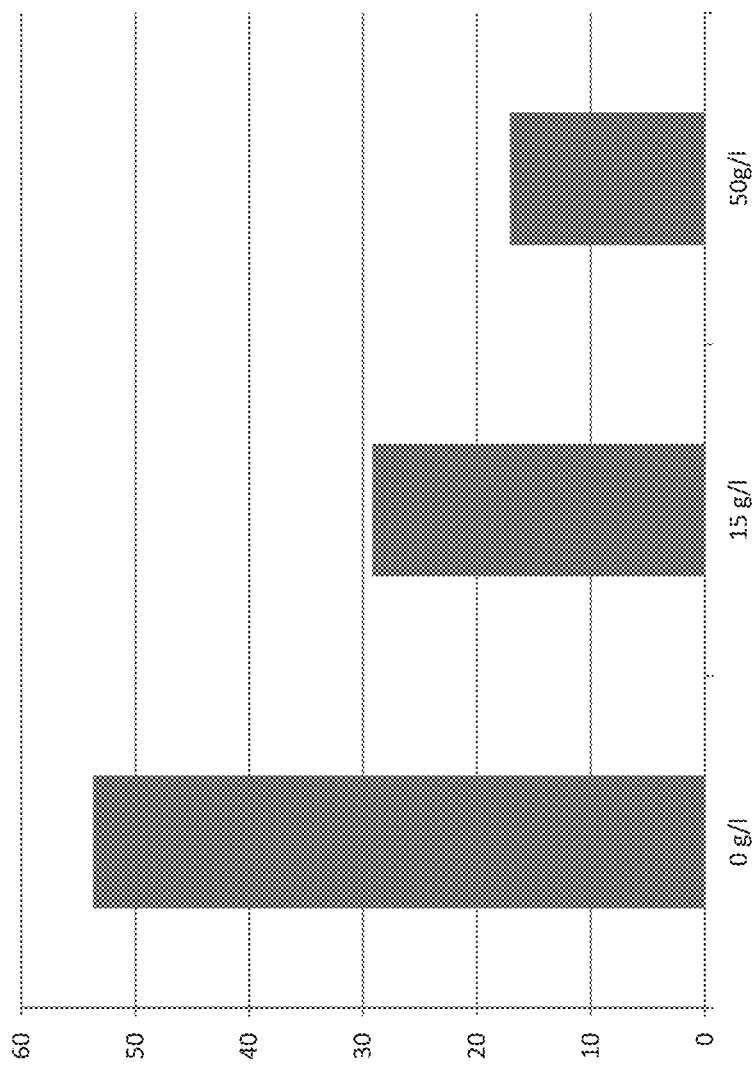
FIG. 3 shows the mean extrusion force of genipin crosslinked gelatin pastes containing 17.5% (w/w) gelatin with various concentrations of human serum albumin in the thrombin component. The x-axis shows the human serum albumin concentration in the thrombin component in [g/l], the y-axis shows the mean extrusion force in [N].
Figure 4:
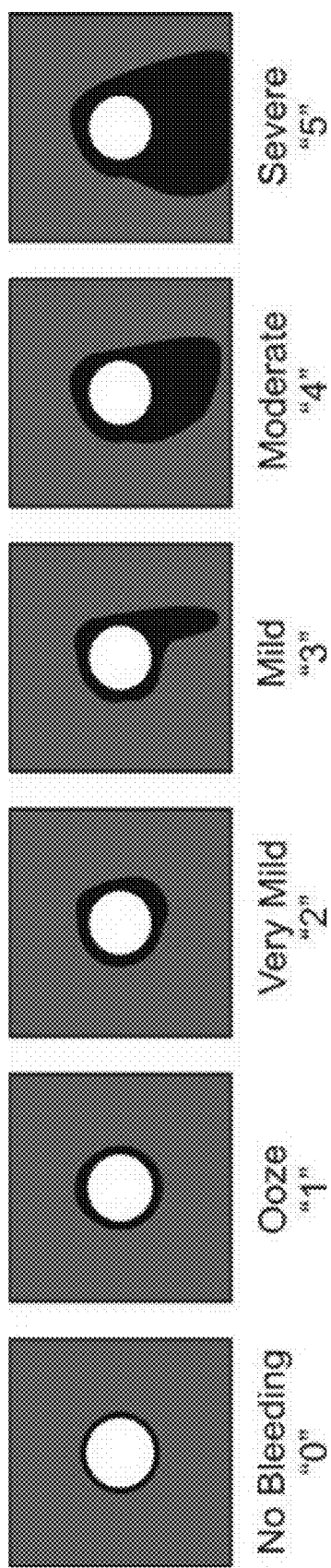
FIG. 4 shows evaluation of bleeding severity post test article application and approximation.

The results for a glutaraldehyde crosslinked gelatin as in Floseal are depicted in FIG. 1 and those for a genipin crosslinked gelatin as described below are depicted in FIG. 3 and also shown as corresponding Table 1 and Table 2. The consistency of crosslinked gelatin pastes containing 17.5% (w/w) crosslinked gelatin depending on the concentration of albumin is shown in FIG. 2 (with 0, 25, 50 and 75 g/l human serum albumin provided in the thrombin component).

TABLE 1

| c(albumin) [g/l] in the thrombin component | extrusion force [N] | std dev |
| --- | --- | --- |
| 0 | 40 | 2.4 |
| 5 | 38 | 1.5 |
| 15 | 30 | 2.6 |
| 25 | 25 | 2.2 |
| 50 | 19 | 1.5 |
| 60 | 19 | 1.0 |

TABLE 2

| c(albumin) g/l in the thrombin component | extrusion force [N] | std dev |
| --- | --- | --- |
| 0 | 54 | 1.9 |
| 15 | 29 | 3.6 |
| 50 | 17 | 2.2 |

Preparation of Genipin Crosslinked Gelatin:

Bovine derived collagen was processed via alkaline treatment and subsequently rinsed with deionized process water (DIW) to remove residual salts. Gelatin was extracted by heat treatment and dried in sheets. The sheets were ground to a powder that was to be processed using genipin as a crosslinking agent.

1 kg of gelatin granules were added to 20 l of a 10 mM genipin solution in DIW. The reaction was performed at neutral pH (7.2) in a jacketed temperature controlled tank at 23° C. Mixing was carried out for 6 hours and the solution was drained off, retaining the solids within a mesh, and rinsed through with DIW to wash out remaining genipin. The material was re-suspended in a 5% $H_2O_2$ solution for 20 hours. The material was rinsed through with DIW to remove the $H_2O_2$. The solids were pre-dried on filter paper under vacuum and then oven dried for 2.5 days. The dried matrix was ground to a powder and filled into individual plastic syringes before exposure to gamma irradiation.

Example 2: Determination of Hemostatic Efficiency

Materials and Methods:
Animal Model

For this model, a midline laparotomy is performed, followed by electrocautery to stop the bleeding from the surgical incision. The liver is exposed and a lobe is isolated. A 10 mm diameter punch biopsy is used to create a series of 2, non-full thickness lesions, approximately 5 mm deep, with the core tissue removed. A pre-treatment assessment is made on the lesion which includes collecting the blood flowing from each lesion for 10 sec. with pre-weighed gauze.

Test articles are randomized and presented to the surgeon who is blinded to the sample treatment. Approximately 1.0 ml of the assigned test article is topically applied to a lesion. Saline moistened gauze is used to help approximate the test articles to their designated lesions, and the timer is started. The saline moistened approximation gauze is removed after 30 seconds.

The degree of bleeding is assessed at 30, 60, 90, 120, 300, and 600 sec. after the test articles are applied to their designated lesions as per the depictions in FIG. 3 (Bleeding score: 0: no bleeding (product saturated with blood); 1: ooze (blood out of product but no blood drop); 2: very mild (blood drop on the product); 3: mild (blood drop streams down); 4: moderate (small amount of blood streams down); 5: severe (large amount of blood streams down)).

Product saturated with blood, but without active bleeding is scored as a "0" (zero). Saline is used to irrigate the excess test articles away from the lesions after the 300 sec. assessment. The procedure is repeated and performed in multiple liver lobes. A single surgeon creates, treats, and performs the observation assessments.

Test Article Synthesis

Test articles for the in vivo evaluation in the porcine-liver model were made by preparing pastes of crosslinked gelatin (in concentrations of 14.5% and 17.5% with 25 or 50 g/l human serum albumin in the thrombin solution (with or without additional 2.5% PEG)).

The results are depicted in FIGS. 5 to 8 showing improved performance with 17.5% gelatin and less effectiveness in the presence of plasticizers (PEG).

Example 3

Gelatin samples were formulated per the package insert for Floseal with a couple key exceptions. First, sodium chloride was used instead of calcium chloride and the gelatin was formulated at 125% solids instead of 100%. The gelatin/thrombin formulations were allowed to stand for 25 minutes and then 1 ml of the preparation was discarded. The other 1 ml of material was applied to the topical hemostasis system (THS). The THS apparatus was previously primed with platelet poor plasma.

The THS is an apparatus designed to simulate a bleeding wound. The artificial wound is a cylindrical hole in a silicone substrate. The surface of the silicone cylinder was coated with a layer of fibrinogen. A syringe pump expelled the clotting fluid (whole blood, plasma, etc.) in this case platelet poor plasma, while the back pressure was recorded. In this experiment the plasma was flowed at a fixed rate of 0.25 ml/min through a small hole at the bottom center of the cylindrical wound. The excess plasma was soaked up with gauze immediately prior to application of the hemostatic matrix. As the plasma continued to flow, 1 ml of the hemostatic matrix was applied to the cylindrical wound. This was immediately covered with wet gauze and a fixed pressure was applied. After 30 seconds the weight was removed and the plasma continued to flow for 8-10 minutes, at which point the flow was stopped and the clot set aside in a humidity chamber where it stayed for more than 2 hours. At the end of the two hours, the clot was mounted onto a vibratome at 8° C., where approximately 500 µm thick slabs were sectioned from the clot. These sections were immersed into a PBS buffer. The slabs were stored in a 5° C. refrigerator when not in use. The slab was placed onto a coverslip and imaged with a Nikon A1R confocal microscope running the NIS-Elements Advanced Research v3.22.00 Build 710 software. To collect micrographs, a plan fluor 10× objective was used with laser excitation light at 488 nm and an emission collection window from 500-550 nm. A transmitted light image was simultaneously collected using a transmitted light detector. With these imaging parameters, automated stitching performed by the software was used to generate macroscopic maps of samples. Smaller areas of the samples were also characterized by collecting 3D z-stacks of images with an optical slice thickness of 5.125 µm. The composite confocal map was used to identify the gelatin granules that are located at the surface, and which were sectioned. This was important for positioning of the elasticity measurement in the atomic force microscope (AFM). The clot slab was mounted in a Veeco Multimode AFM. The multimode was equipped with a Nanoscope V controller and a JV piezoelectric scanner. The force measurements were made with a Novascan AFM cantilever which supported a 4.5 µm polystyrene sphere. The cantilever's force constant was determined to be 0.779 N/m by the thermal tune method. The cantilever was positioned above the center of the gelatin granule, and then a 16×16 array of force measurements were made. Each force curve involved moving the gelatin granule up into contact with the polystyrene sphere, and continuing to move the granule up until the cantilever deflection reached a preset trigger value of 2 volts, at which point the gelatin was retracted a distance of 1.00 micron from the trigger location.

DISCUSSION

The fluorescence data shows that the glutaraldehyde crosslinked gelatin is not uniformly crosslinked. Instead, the crosslinking density seems higher around the edges of the granules, with the central portion of the granule being significantly less crosslinked than the edges. In contrast, the genipin crosslinked gelatin appears uniformly (homogeneously) crosslinked throughout the granules. There are no substantial edge effects to the fluorescence intensity. The fluorescence intensity of the genipin and glutaraldehyde crosslinked materials cannot be directly compared, because of the potential fluorescence differences attributed to the crosslinkers themselves. However, the AFM measured elastic modulus measurement show that the genipin crosslinked gelatin is stiffer than the glutaraldehyde crosslinked gelatin, which appears to be softer (more flexible).

The invention claimed is:

1. A hemostatic composition comprising crosslinked gelatin in particulate form suitable for use in hemostasis and albumin as an extrusion enhancer, wherein the composition is present in paste form containing 15.0 to 19.5% (w/w) crosslinked gelatin and 0.5 to 5.0% (w/w) extrusion enhancer, wherein the composition is present in a syringe, wherein the hemostatic composition has a mean extrusion force of 40 N or lower, wherein the hemostatic composition is free of polyethylene glycol, sorbitol, and glycerol, wherein (w/w) crosslinked gelatin is defined as the weight of dry crosslinked gelatin per weight of the hemostatic composition, and wherein (w/w) extrusion enhancer is defined as the weight of extrusion enhancer per weight of the hemostatic composition.

2. The hemostatic composition according to claim 1, wherein the crosslinked gelatin is glutaraldehyde-crosslinked gelatin or genipin-crosslinked gelatin.

3. The hemostatic composition according to claim 1, wherein the crosslinked gelatin is type B gelatin.

4. The hemostatic composition according to claim 1, wherein the crosslinked gelatin is present as granular material.

5. The hemostatic composition according to claim 1, wherein the crosslinked gelatin has a mean particle size of 100 to 1000 µm.

6. The hemostatic composition according to claim 1, wherein the composition contains thrombin.

7. The hemostatic composition to claim 1 for use in the treatment of an injury selected from the group consisting of a wound, a hemorrhage, a damaged tissue, a bleeding tissue, and a bone defect.

8. The hemostatic composition according to claim 1, wherein the composition contains 16.0 to 19.5% (w/w) crosslinked gelatin.

9. The hemostatic composition according to claim 1, wherein the composition contains 16.5 to 19.5% (w/w) crosslinked gelatin.

10. The hemostatic composition according to claim 1, wherein the composition contains 16.5 to 19.0% (w/w) crosslinked gelatin.

11. The hemostatic composition according to claim 1, wherein the composition contains 17.0 to 18.5% (w/w) crosslinked gelatin.

12. The hemostatic composition according to claim 1, wherein the composition contains 16.5 to 17.5% (w/w) crosslinked gelatin.

13. The hemostatic composition according to claim 1, wherein the composition has a mean extrusion force of 35 N or lower.

14. The hemostatic composition according to claim 1, wherein the composition has a mean extrusion force of 20 N or lower.

15. The hemostatic composition according to claim 1, wherein the composition is characterized by a mean extrusion force of 40 N or lower, wherein mean extrusion force corresponds to a force required to extrude the hemostatic composition from a 5 ml standard syringe having a cylindrical body with an inner diameter of 12.2 mm coupled with a luer having an inner nozzle lumen diameter of 2.54 mm, using a 100 N load cell operating at a cross-beam speed of 250 mm/min with a cross-beam displacement of 34 mm.

16. The hemostatic composition according to claim 1, wherein the albumin extrusion enhancer is included in the paste at a concentration of between 1% and 5% (w/w).

17. The hemostatic composition according to claim 1, wherein the albumin extrusion enhancer is included in the paste at a concentration of between 2% and 4.5% (w/w).

18. The hemostatic composition according to claim 1, wherein the albumin extrusion enhancer is included in the paste at a concentration of between 1.5% and 5% (w/w).

19. The hemostatic composition according to claim 1, wherein the albumin extrusion enhancer is included in the paste at a concentration of about 1.5% (w/w).

20. The hemostatic composition according to claim 1, wherein the albumin extrusion enhancer is included in the paste at a concentration of between 0.8% and 3.3% (w/w).

21. The hemostatic composition according to claim 1, wherein the composition has a mean extrusion force in the range of 15 to 30 N.

22. A kit for making a flowable paste of crosslinked gelatin for the treatment of an injury selected from the group consisting of a wound, a hemorrhage, a damaged tissue, and a bleeding tissue, comprising:
 a) a dry hemostatic composition comprising crosslinked gelatin in particulate form to be reconstituted to a flowable paste containing 15.0 to 19.5% (w/w) crosslinked gelatin, wherein (w/w) crosslinked gelatin is defined as the weight of dry crosslinked gelatin per weight of the flowable paste; and
 b) a pharmaceutically acceptable diluent for reconstitution of the hemostatic composition,
 wherein either the composition or the diluent comprises albumin in an amount which leads to an albumin concentration in the reconstituted paste of between 0.5 to 5.0% (w/w), wherein (w/w) albumin is defined as the weight of albumin per weight of the hemostatic composition, wherein the reconstituted paste has a mean extrusion force of 40 N or lower, and wherein the reconstituted paste is free of polyethylene glycol, sorbitol, and glycerol.

23. The kit according to claim 22, wherein the pharmaceutically acceptable diluent comprises a buffer or buffer system.

24. The kit according to claim 22, wherein the pharmaceutically acceptable diluent comprises thrombin.

25. The kit according to claim 22, wherein the pharmaceutically acceptable diluent contains a substance selected from the group consisting of NaCl, $CaCl_2$, and sodium acetate.

26. A method of treating an injury selected from the group consisting of a wound, a hemorrhage, a damaged tissue, and a bleeding tissue, comprising administering a hemostatic composition according to claim 1 to the injury.

27. A method for providing a ready to use form of a hemostatic composition according to claim 1, wherein the hemostatic composition is provided in a first syringe and a diluent for reconstitution is provided in a second syringe, the first and the second syringe are connected to each other, and the fluid is brought into the first syringe to produce a flowable form of the hemostatic composition.

28. The method according to claim 27, wherein the flowable form of the hemostatic composition contains particles, where more than 50% (w/w) of the particles have a size of 100 to 1000 µm.

* * * * *